US012778555B2

(12) United States Patent
Nally et al.

(10) Patent No.: US 12,778,555 B2
(45) Date of Patent: Nov. 3, 2026

(54) ULTRASOUND PROBE WITH INTEGRATED CONTROLS

(71) Applicant: FUJIFILM SONOSITE, INC., Bothell, WA (US)

(72) Inventors: Patrick Nally, Seattle, WA (US); Tyler Dawson, Edmonds, WA (US); Kenji Kimura, Seattle, WA (US); David Knapp, Bellevue, WA (US); Floris Kruger, Bothell, WA (US); Lisa Spencer, Bothell, WA (US); Craig Chamberlain, Seattle, WA (US); Brittney Klingenberg, Bothell, WA (US); Laurie Johnson, North Bend, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

(21) Appl. No.: 19/262,490

(22) Filed: Jul. 8, 2025

(65) Prior Publication Data

US 2025/0331823 A1 Oct. 30, 2025

Related U.S. Application Data

(63) Continuation of application No. 18/071,416, filed on Nov. 29, 2022, now Pat. No. 12,514,555.

(Continued)

(51) Int. Cl.

| | |
|---|---|
| ***A61B 8/00*** | (2006.01) |
| ***A61B 8/12*** | (2006.01) |
| ***A61B 90/00*** | (2016.01) |

(52) U.S. Cl.

CPC ................ *A61B 8/463* (2013.01); *A61B 8/12* (2013.01); *A61B 8/4209* (2013.01); *A61B 8/4254* (2013.01); *A61B 8/4411* (2013.01); *A61B 8/461* (2013.01); *A61B 8/467* (2013.01); *A61B 8/546* (2013.01); *A61B 2090/036* (2016.02)

(58) Field of Classification Search

CPC ......... A61B 8/463; A61B 8/12; A61B 8/4209; A61B 8/4254; A61B 8/4411; A61B 8/461; A61B 8/467; A61B 8/546; A61B 2090/036; A61B 8/4405; A61B 8/56; A61B 8/469;

(Continued)

(56) References Cited

U.S. PATENT DOCUMENTS

| | | |
|---|---|---|
| 4,531,844 A | 7/1985 | Juras |
| 5,390,661 A | 2/1995 | Griffith et al. |

(Continued)

OTHER PUBLICATIONS

Final Office Action received for U.S. Appl. No. 18/071,416, mailed on Dec. 9, 2024, 55 pages.

(Continued)

*Primary Examiner* — Kaitlyn E Sebastian

(74) *Attorney, Agent, or Firm* — Womble Bond Dickinson (US) LLP

(57) ABSTRACT

An ultrasound probe and an ultrasound system are disclosed. In some embodiments, the ultrasound probe includes a probe body having a user interface with controls and a mode selector. In some embodiments, when the mode selector is in a first setting, the controls are configured to control a probe transducer, and when the mode selector is in a second setting, the controls are configured to control the ultrasound machine via a probe transceiver.

20 Claims, 25 Drawing Sheets

Related U.S. Application Data

(60) Provisional application No. 63/283,893, filed on Nov. 29, 2021, provisional application No. 63/283,897, filed on Nov. 29, 2021.

(58) Field of Classification Search
CPC ..... A61B 8/4455; A61B 8/4444; A61B 8/445; A61B 8/465; A61B 8/54
See application file for complete search history.

(56) References Cited

U.S. PATENT DOCUMENTS

| | | | | |
|---|---|---|---|---|
| 2003/0073894 | A1* | 4/2003 | Chiang | A61B 8/56 600/407 |
| 2004/0002652 | A1 | 1/2004 | Phelps et al. | |
| 2005/0283078 | A1* | 12/2005 | Steen | A61B 8/463 600/447 |
| 2007/0093713 | A1* | 4/2007 | Byron | A61B 8/461 600/437 |
| 2012/0157843 | A1 | 6/2012 | Lavin et al. | |
| 2013/0253327 | A1 | 9/2013 | Ko et al. | |
| 2014/0121524 | A1* | 5/2014 | Chiang | A61B 8/4427 600/459 |
| 2016/0266069 | A1 | 9/2016 | Jenkins | |
| 2017/0281029 | A1 | 10/2017 | Messerly et al. | |
| 2018/0059061 | A1* | 3/2018 | Scaccabarozzi | G01N 29/262 |
| 2020/0022678 | A1* | 1/2020 | McLaughlin | A61B 8/54 |
| 2020/0169046 | A1 | 5/2020 | Kanakasabhapathi et al. | |
| 2021/0100530 | A1* | 4/2021 | Park | A61B 5/4523 |
| 2022/0304660 | A1* | 9/2022 | Loype | A61B 8/54 |

OTHER PUBLICATIONS

Non-Final Office Action received for U.S. Appl. No. 18/071,416, mailed on Jun. 25, 2024, 48 pages.
Non-Final Office Action received for U.S. Appl. No. 18/071,420, mailed on Feb. 6, 2025, 10 pages.
Notice of Allowance received for U.S. Appl. No. 18/071,416, mailed on Apr. 30, 2025, 17 pages.
Notice of Allowance received for U.S. Appl. No. 18/071,420, mailed on Apr. 7, 2025, 6 pages.
Notice of Allowance received for U.S. Appl. No. 18/071,420, mailed on Mar. 31, 2025, 8 pages.
Requirement for Restriction/Election received for U.S. Appl. No. 18/071,420, mailed on Nov. 8, 2024, 7 pages.

* cited by examiner

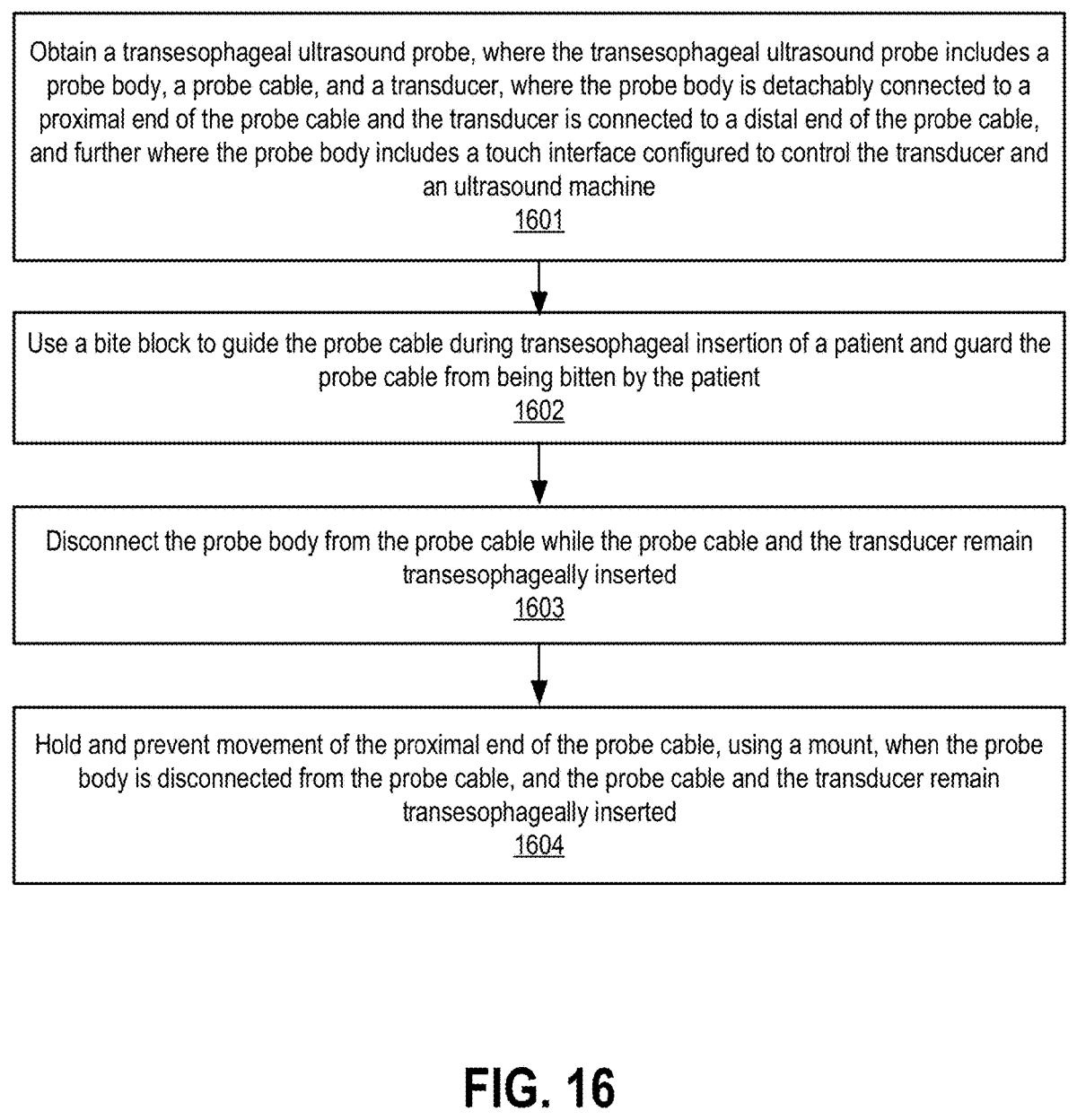

Obtain a transesophageal ultrasound probe, where the transesophageal ultrasound probe includes a probe body, a probe cable, and a transducer, where the probe body is detachably connected to a proximal end of the probe cable and the transducer is connected to a distal end of the probe cable, and further where the probe body includes a touch interface configured to control the transducer and an ultrasound machine
1601

Use a bite block to guide the probe cable during transesophageal insertion of a patient and guard the probe cable from being bitten by the patient
1602

Disconnect the probe body from the probe cable while the probe cable and the transducer remain transesophageally inserted
1603

Hold and prevent movement of the proximal end of the probe cable, using a mount, when the probe body is disconnected from the probe cable, and the probe cable and the transducer remain transesophageally inserted
1604

FIG. 16

ULTRASOUND PROBE WITH INTEGRATED CONTROLS

RELATED APPLICATION

The present application is a continuation of U.S. patent application Ser. No. 18/071,416, filed Nov. 29, 2022, entitled "ULTRASOUND PROBE WITH INTEGRATED CONTROLS" that claims the benefit of U.S. Provisional Patent Application No. 63/283,893, filed Nov. 29, 2021, entitled "ULTRASOUND PROBE WITH INTEGRATED CONTROLS", and U.S. Provisional Patent Application No. 63/283,897, filed Nov. 29, 2021, entitled "TRANSESOPHAGEAL ULTRASOUND SYSTEM" that are incorporated by reference herein in their entirety.

FIELD OF THE INVENTION

Embodiments disclosed herein relate generally to ultrasound imaging; more specifically, the embodiments disclosed herein relate to an ultrasound probe for use in performing transesophageal echocardiogram (TEE) ultrasound or other ultrasound procedures with an ultrasound imaging system.

BACKGROUND

TEE ultrasound uses a specialized probe inserted in a patient's throat to capture unobstructed views of the patient's heart. These specialized TEE probes have been used for many years to perform transesophageal ultrasound. One such TEE probe was first patented in 1997 and remains largely unchanged since that time, relying on a basic mechanical cabling system with knobs to control the movement of the probe. The use of the knobs is inherently cumbersome and unintuitive.

SUMMARY

An ultrasound probe and ultrasound system for using the same are disclosed. In some embodiments, the ultrasound probe comprises a transesophageal ultrasound probe and the ultrasound system comprises a transesophageal ultrasound system. In some embodiments, the ultrasound probe includes a transceiver configured to communicatively couple the ultrasound probe to an ultrasound machine; a probe body having a user interface with controls and a mode selector, and a transducer coupled to the probe body. In some embodiments, when the mode selector is in a first setting, the controls are configured to control the transducer, and when the mode selector is in a second setting, the controls are configured to control the ultrasound machine via the transceiver.

In some embodiments, an ultrasound system includes an ultrasound machine having a user interface configured to display an ultrasound image based on ultrasound data, and an ultrasound probe communicatively coupled to the ultrasound machine and configured to generate the ultrasound data. In some embodiments, the ultrasound probe has a probe body with a touch interface having controls and a mode selector and a transducer coupled to the probe body. In some embodiments, when the mode selector is in a first setting, the controls are configured to control the transducer, the touch interface is configured to indicate the controls with first indicators, and the user interface is configured to display a graphic of the touch interface having the first indicators. In some embodiments, when the mode selector is in a second setting, the controls are configured to control the ultrasound machine, the touch interface is configured to indicate the controls with second indicators, and the user interface is configured to display a graphic of the touch interface having the second indicators.

In some embodiments, the ultrasound system includes an ultrasound machine having a user interface configured to display an ultrasound image based on ultrasound data, and an ultrasound probe communicatively coupled to the ultrasound machine and configured to generate the ultrasound data. In some embodiments, the ultrasound probe has a probe body with a touch interface having controls and a mode selector, an ultrasound cable, and a transducer at one end of the ultrasound cable and coupled to the probe body via the ultrasound cable. In some embodiments, when the mode selector is in a first setting, the controls are configured to control a flexion angle of the transducer relative to the probe cable, and the user interface is configured to display an indicator of the flexion angle.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 16 is a data flow diagram of some embodiments of process for performing an ultrasound examination.

DETAILED DESCRIPTION

Figure 1:
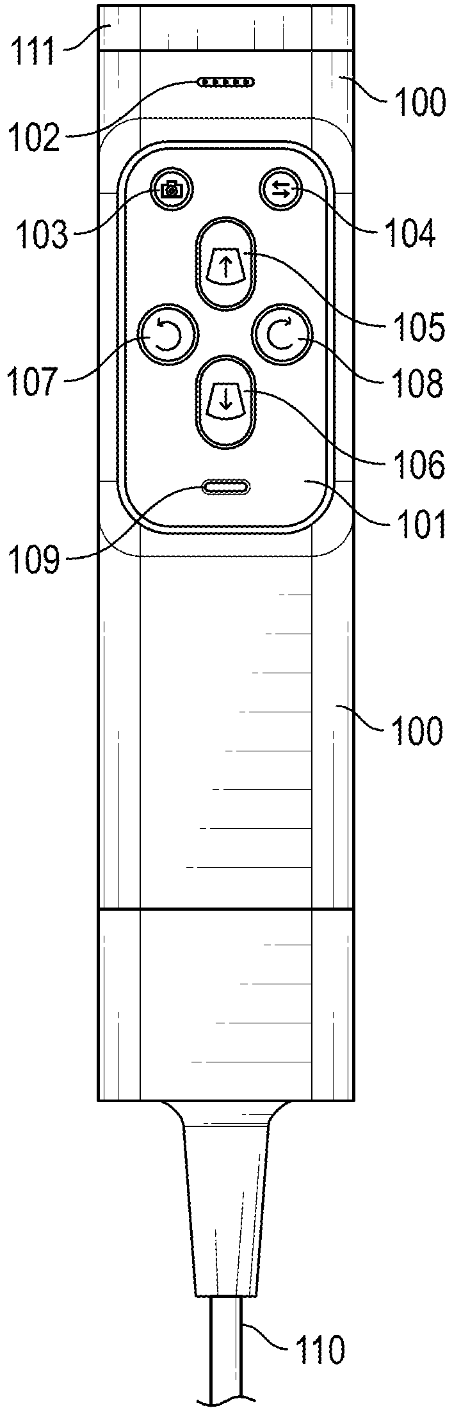
FIG. 1 illustrates some embodiments of a probe of an ultrasound system.

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

A transesophageal ultrasound system is disclosed. In some embodiments, the transesophageal ultrasound system includes a transesophageal ultrasound probe including a probe body, a probe (transducer) cable and a transducer coupled to the probe body via the probe cable. The transducer cable is configured for esophageal insertion. In some embodiments, the ultrasound probe is communicatively coupled to an ultrasound machine that is configured to generate ultrasound data. Note that while many of the probe and ultrasound system features disclosed herein are described for use in a transesophageal ultrasound system, these features may also be part of other ultrasound systems.

In some embodiments, the ultrasound probe includes a probe body having a user interface with controls. In some embodiments, the user interface with controls includes a probe control panel with a touch surface interface. In some embodiments, the touch surface interface includes capacitive sensors configured to sense the locations proximate to the touch surface interface. These locations may include button locations to guide a user to touch certain locations on the touch interface to activate individual controls. In some embodiments, the controls of the touch interface of the probe control panel include a first set of controls for controlling the transducer of the probe and a second set of controls for controlling the ultrasound imaging performed by the ultrasound system based on ultrasound signals returned from the probe. In some embodiments, the tip of the transducer is configured to move at an angle relative to the probe cable based on the controls selected by the user.

In some embodiments, the two sets of controls are part of two different modes of operation for the probe. The user is able to switch between the two modes to use each of the two sets of controls. In some embodiments, the user switches between the modes and the sets of controls using a mode selector. In some embodiments, the mode selector is in the form of a mode button on the touch interface of the probe and switching between the modes is performed by activating or otherwise touching (e.g., pressing) the mode button. In some embodiments, selecting the mode button controls the probe to arbitrate between ultrasound controls and TEE probe controls. The probe may include feedback information to indicate in which mode the probe is currently configured. For example, in some embodiments, lights or other illumination features on the probe (and on the display screen of the ultrasound system) change to communicate the mode status to a user.

In some embodiments, in a first mode setting, the controls of the touch interface control the transducer of the ultrasound probe, and in a second mode setting, the touch interface controls are configured to control the ultrasound machine. In some embodiments, in the first mode setting, the controls are configured to control the anteflexion and retroflexion of the transducer and to control the omniplane left and omniplane right ultrasound transmission of the transducer (which controls an omniplane angle of the ultrasound transmitted by the transducer). In some embodiments, the touch interface is configured to indicate the controls of the first mode setting with first indicators on the user interface. In some embodiments, in such a case, the touch interface is configured to indicate the controls with a first set of indicators (e.g., graphics on buttons on the touch interface). In some embodiments, in the second mode setting, the controls of the touch interface control imaging characteristics of the ultrasound images (e.g., the depth and gain of the ultrasound machine). In some embodiments, in such a case, the touch interface is configured to indicate these controls with a second set of indicators (e.g., graphics on buttons on the touch interface).

FIG. 1 illustrates some embodiments of a probe of an ultrasound system. Referring to FIG. 1, probe 100 is coupled to a probe cable 110 that includes a transducer. In one embodiment, probe 100 comprises a transesophageal ultrasound probe and the transducer is controlled to perform TEE operations. A battery 111 provides power to probe 100 and its status is indicated on probe 100 using battery indicator 102.

In some embodiments, probe 100 includes control panel 101 with controls for both TEE operation of the probe transducer and controls for controlling an ultrasound machine. For TEE operation, the probe 100 includes probe cable 110 that is coupled to a probe tip or endpoint that is controlled with the controls on control panel 101.

In some embodiments, control panel 101 of the probe includes a touch interface with controls that include a save button 103, a reset button 109, and a mode switch button 104. Save button 103 may be used to save an image being displayed on an ultrasound machine generated as a result of ultrasound data from the probe. A reset button 109 resets the probe tip that is at the end of probe cable 110. The resetting of the probe tip may include returning the probe tip to a limp or neutral state. In some embodiments, reset button 109 sits flush with the surface of probe 100 to avoid being inadvertently pressed during the scan operation using probe 100.

Mode switch button 104 is used by the user as a mode selector to switch between two sets of controls, a first set for controlling transducer operation of the probe transducer (e.g., TEE operation of the transducer, etc.) in a first mode and a second set for controlling the imaging being performed by an ultrasound machine in a second mode. In some embodiments, selecting the mode switch button 104 on control panel 101 allows the user to switch between controlling the probe transducer using TEE controls of the ultrasound probe and using the probe for controlling ultrasound image characteristics of the ultrasound machine. In some embodiments, the image characteristics controllable through the probe are gain and depth. However, the techniques described herein are not limited to controlling the depth and gain of ultrasound images and may be used to control other imaging parameters.

If mode switch button 104 is set to operate the probe with the first set of controls in the first mode, control panel 101 additionally includes anteflexion button 105, retroflexion button 106, omniplane left button 107 and omniplane right button 108. In some embodiments, the anteflexion button 105 and the retroflexion button 106 are vertically aligned to provide a more intuitive arrangement for the user. Omniplane left button 107 and omniplane right button 108 are oriented on each side of the flexion button controls to enable a user to keep a more natural mental model of the probe while in the body.

Figure 2A:
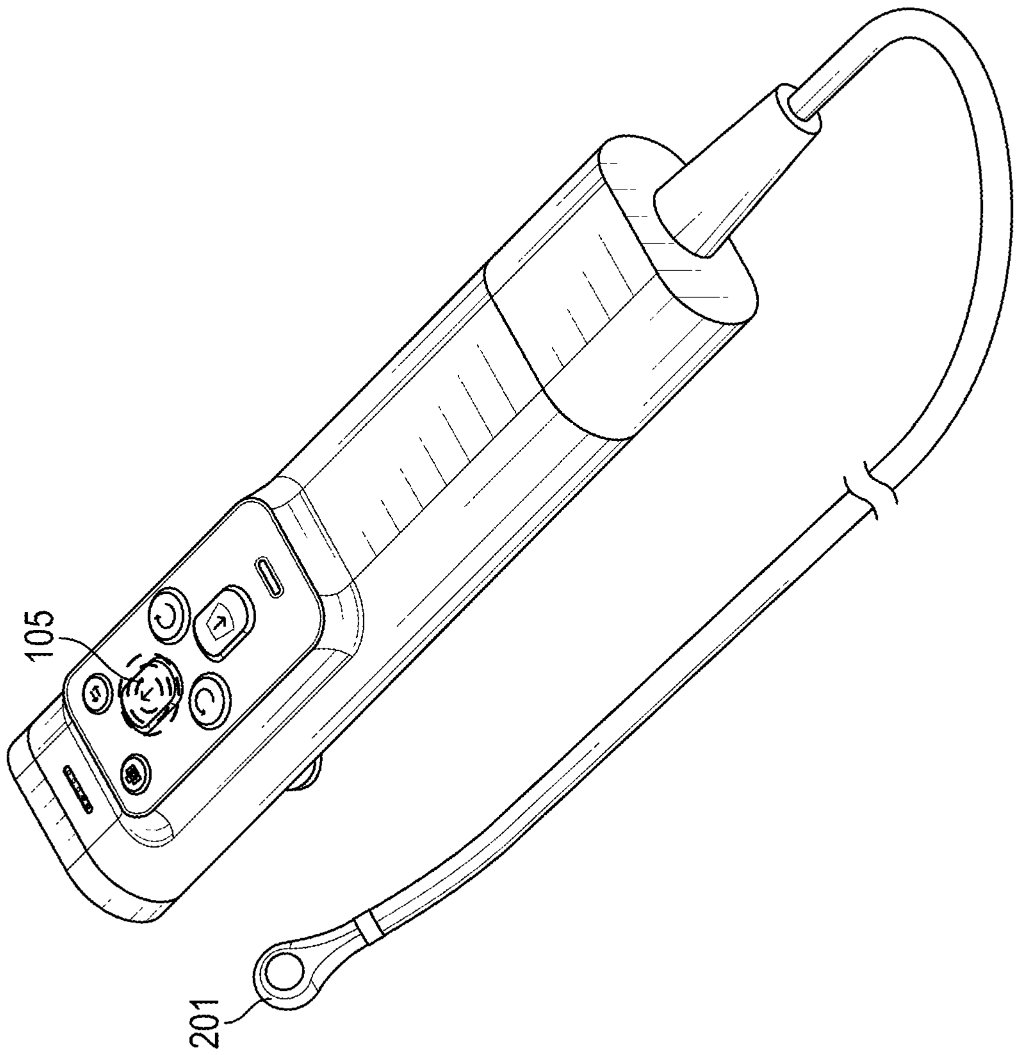
FIGS. 2A-2E illustrate movements of a probe tip using the touch interface control panel of some embodiments of a probe.
Figure 2B:
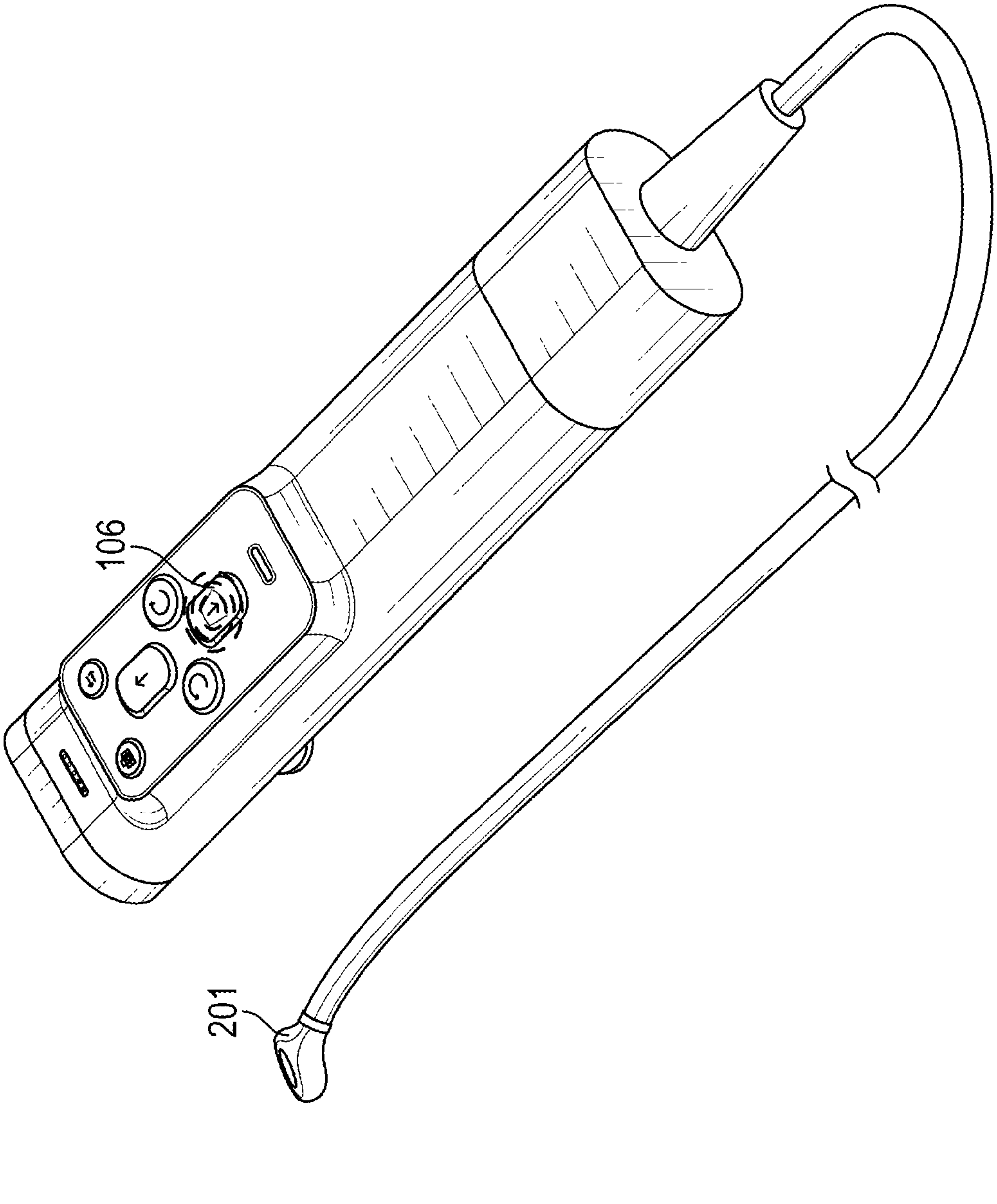
Figure 2C:
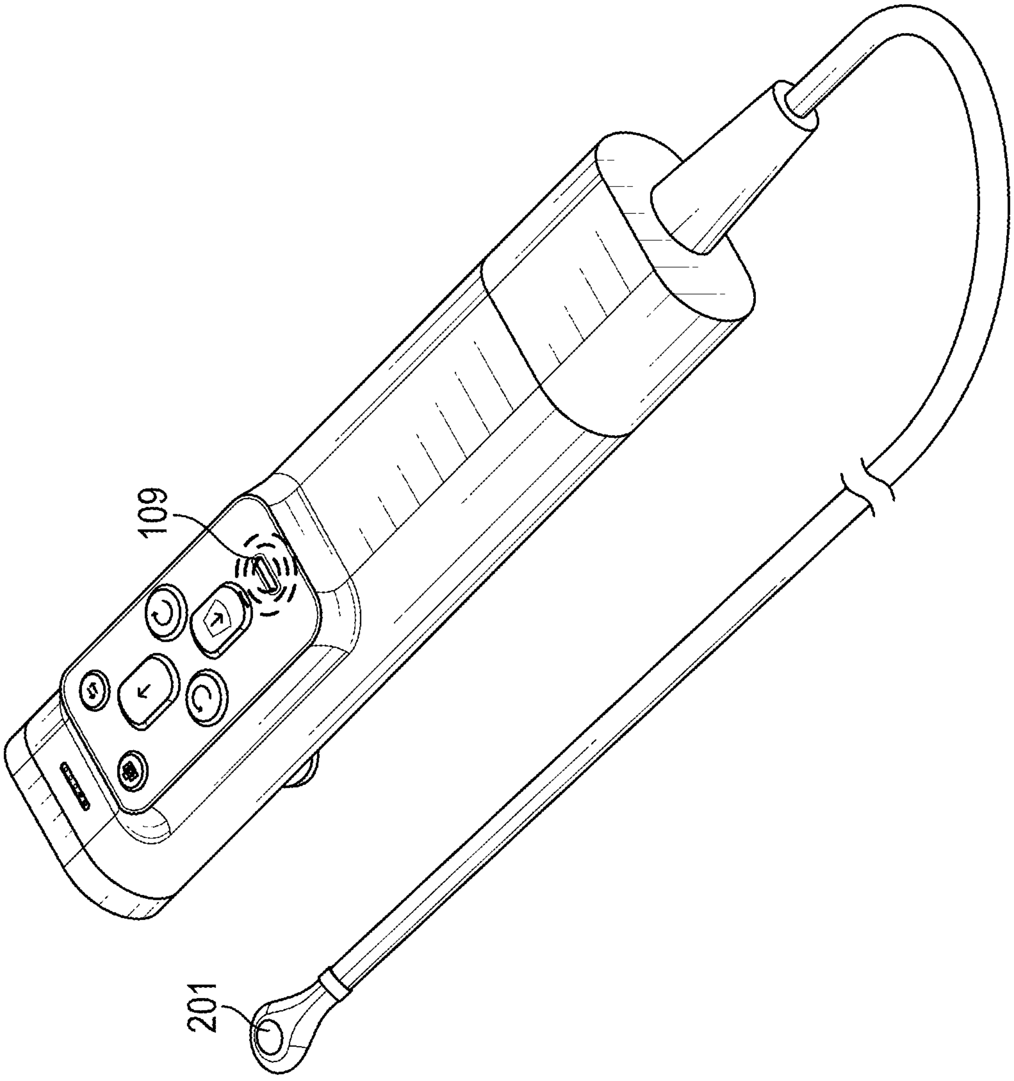
Figure 2D:
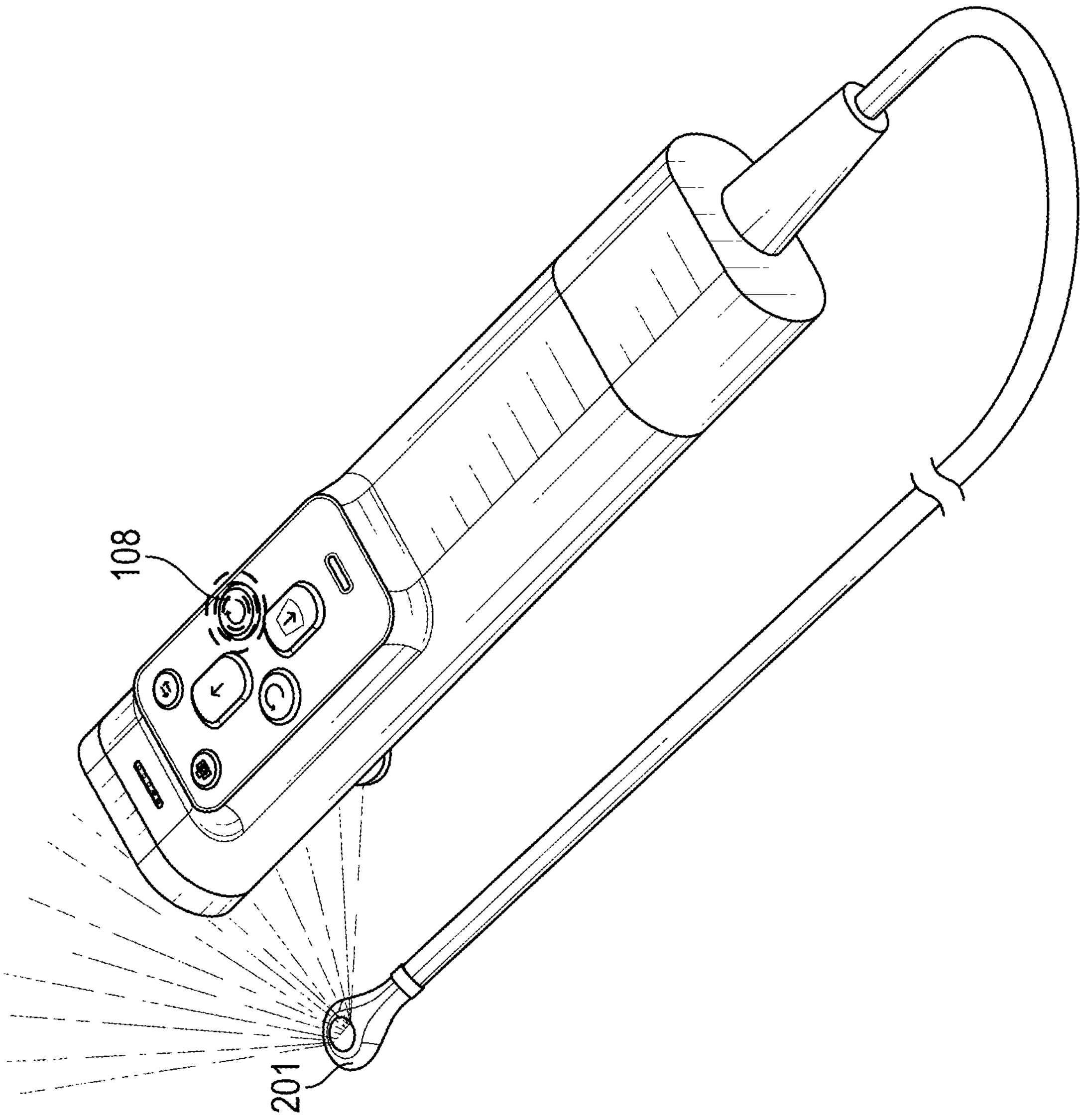
Figure 2E:
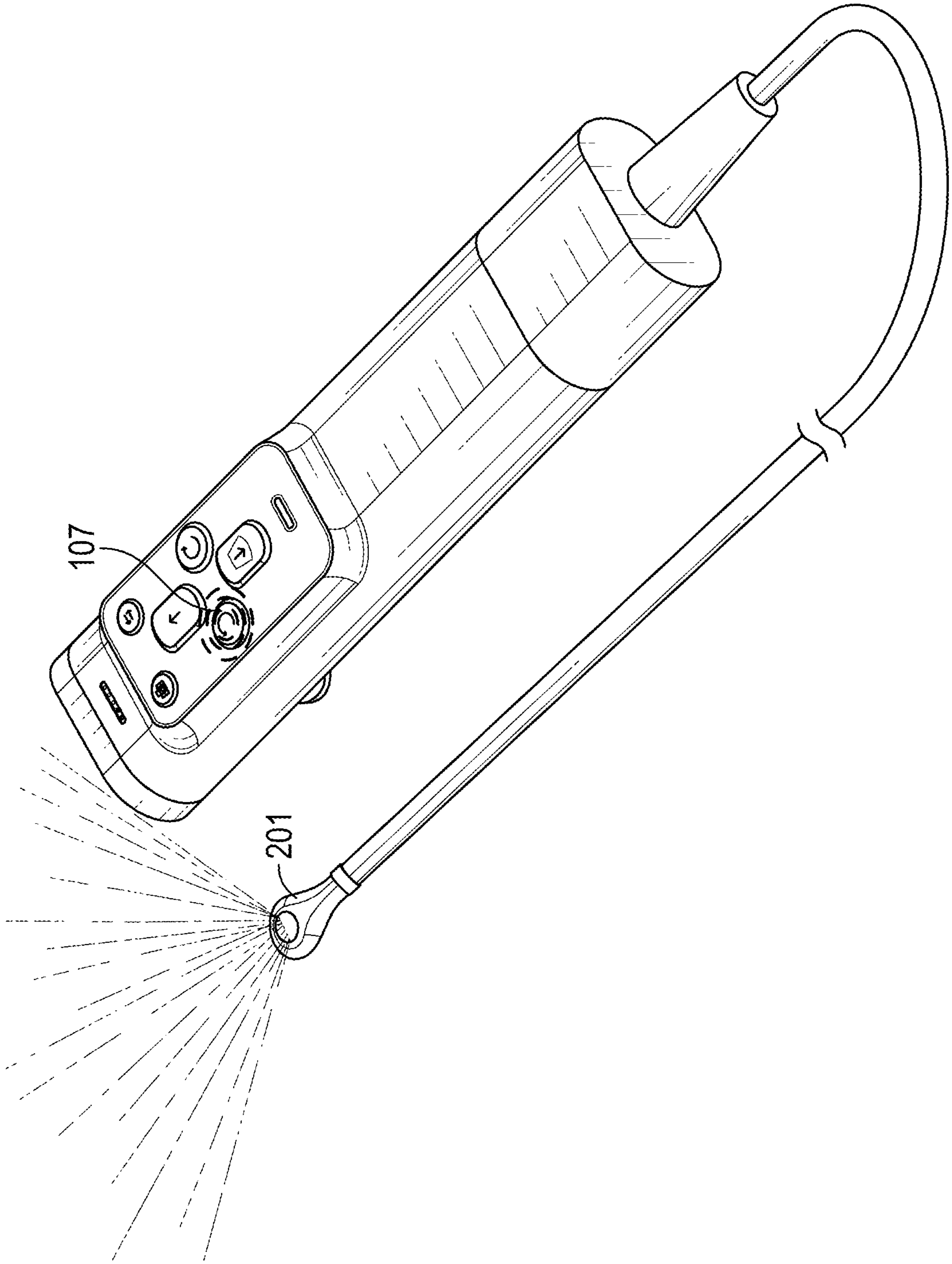

FIGS. 2A-2E illustrate movements of a probe tip using the touch interface control panel of some embodiments of a probe, such as probe 100 of FIG. 1. More specifically, FIG. 2A illustrates the movement of the probe tip in response to activating the anteflexion button (e.g., anteflexion button 105 of FIG. 1). Referring to FIG. 2A, probe tip 201 moves in the anteflexion direction in response to pressing the anteflexion button on the control panel of a probe. FIG. 2B illustrates the movement of the probe tip in response to activating the retroflexion button (e.g., retroflexion button 106 of FIG. 1). Referring to FIG. 2B, probe tip 201 moves in the retroflexion direction in response to activating the retroflexion button on a control panel of a probe. FIG. 2C illustrates the result of the movement of a probe tip in response to activating the reset button on the control panel of a probe. Referring to FIG. 2C, in response to a user pressing reset button 109, probe tip 201 mechanically returns to a default angle relative to the transducer cable when activated (e.g., returning to a neutral position from the anteflexion angled position or returning to a neutral position from the retroflexion angled position). FIG. 2D illustrates one embodiment of the movement of the probe tip in response to activating the omniplane right button on the control panel of an ultrasound probe. Referring to FIG. 2D, in response to activating an omniplane right button (e.g., omniplane right button 108 of FIG. 1), the probe tip 201 rotates to the right. FIG. 2E illustrates one embodiment of a probe after activating the omniplane left button (e.g., omniplane left button 107 of FIG. 1). Referring to FIG. 2E, in response to the user activating the omniplane left button, probe tip 201 rotates to the left.

Note that in some embodiments, the movements of the transducer in response to activation of the buttons on the probe control panel are made mechanically. In some embodiments, the mechanical movements are made via a motor module within the transducer probe.

In some embodiments, the probe body is operable to generate haptic feedback for the user that mimics the mechanical resistance of a cable mechanism. In some embodiments, the probe measures the motor reverse torque and supplies haptic and/or audio feedback based on the resistance encountered determined from the motor reverse torque.

In some embodiments, the transesophageal ultrasound probe includes a temperature sensor configured to determine the temperature of the transducer. In some embodiments, the ultrasound machine includes a user interface configured to display the temperature. The ultrasound machine may receive information indicative of the sensed temperature from the transesophageal ultrasound probe wirelessly from a transceiver in the transesophageal ultrasound probe.

In some embodiments, when mode switch button 104 is activated to switch to the second set of settings, the probe may be used to control the ultrasound machine. In some embodiments, these controls are sent via a transceiver (e.g., a transceiver for wireless communication) in the ultrasound probe to the ultrasound machine. In some embodiments, these controls include one or more controls configured to control depth and gain of the ultrasound machine. In some embodiments, when the mode selector is in the second setting, the user interface of control panel 101 is configured to illuminate a portion of the user interface to indicate the control of the depth and gain of the ultrasound machine. In some embodiments, this illumination includes lighting around the control panel or changing the existing lighting of the control panel from one color to another to indicate the mode in which the probe is currently operating. Note that other feedback mechanisms (e.g., audio, vibration, etc.) may be used to provide such feedback instead of or in addition to the use of illumination.

Figure 3:
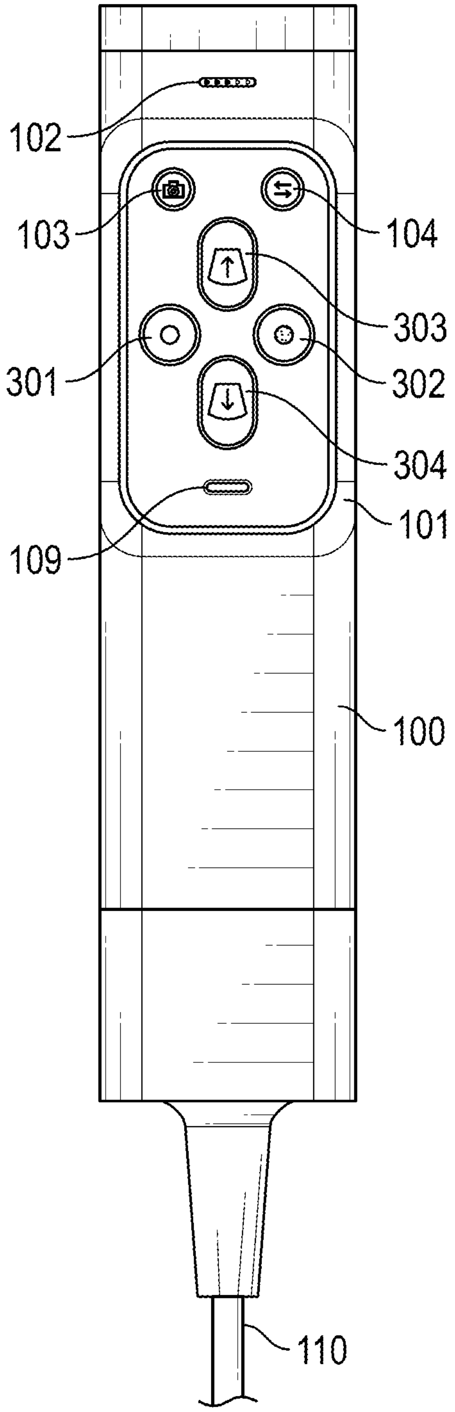
FIG. 3 illustrates some embodiments of the ultrasound system controls that appear on the control panel when the user has switched modes.

FIG. 3 illustrates some embodiments of the controls that appear on the control panel when the user has switched modes to the second set of controls for controlling the image characteristics of the ultrasound imaging. Referring to FIG. 3, control panel 101 has depth controls for increasing and decreasing the depth and gain controls for increasing and decreasing the gain. In some embodiments, in response to the activating mode switch button 104, anteflexion button 105 becomes decrease depth button 303 which may be used, upon activation, to reduce the depth associated with the ultrasound image, retroflexion button 106 changes to an increase depth button 304 that enables the user, upon activation, to increase the depth associated with the ultrasound image, omniplane left button 107 becomes decrease gain button 301 that enables the user, upon activation, to reduce the gain of the ultrasound image. Also in response to pressing the mode switch button 104, omniplane right button 108 becomes increase gain button 302 that enables the user, upon activation, to increase the gain of the ultrasound image. In alternative embodiments, other imaging controls can appear on the touch interface of control panel 101. Examples of other such imaging controls include, but are not limited to, examination type (preset), imaging mode (e.g., B, M, C), neural network selection/activation, save clip (as opposed to saving an image), toggle to next step in a protocol, etc. In some embodiments, one or more buttons on user control panel 101 are user-configurable buttons that the user can map to a selected function or choice.

In some embodiments, the ultrasound probe comprises a transceiver configured to communicatively couple the ultrasound probe to an ultrasound machine. In some embodiments, the transceiver is configured to implement a wireless communication link to communicatively couple the ultrasound probe to the ultrasound machine. The wireless link is used to send ultrasound data from the ultrasound probe to the ultrasound machine as well as imaging control signals (e.g., gain control signals, depth control signals, etc.) that are selected by the user using the probe.

Figure 4:
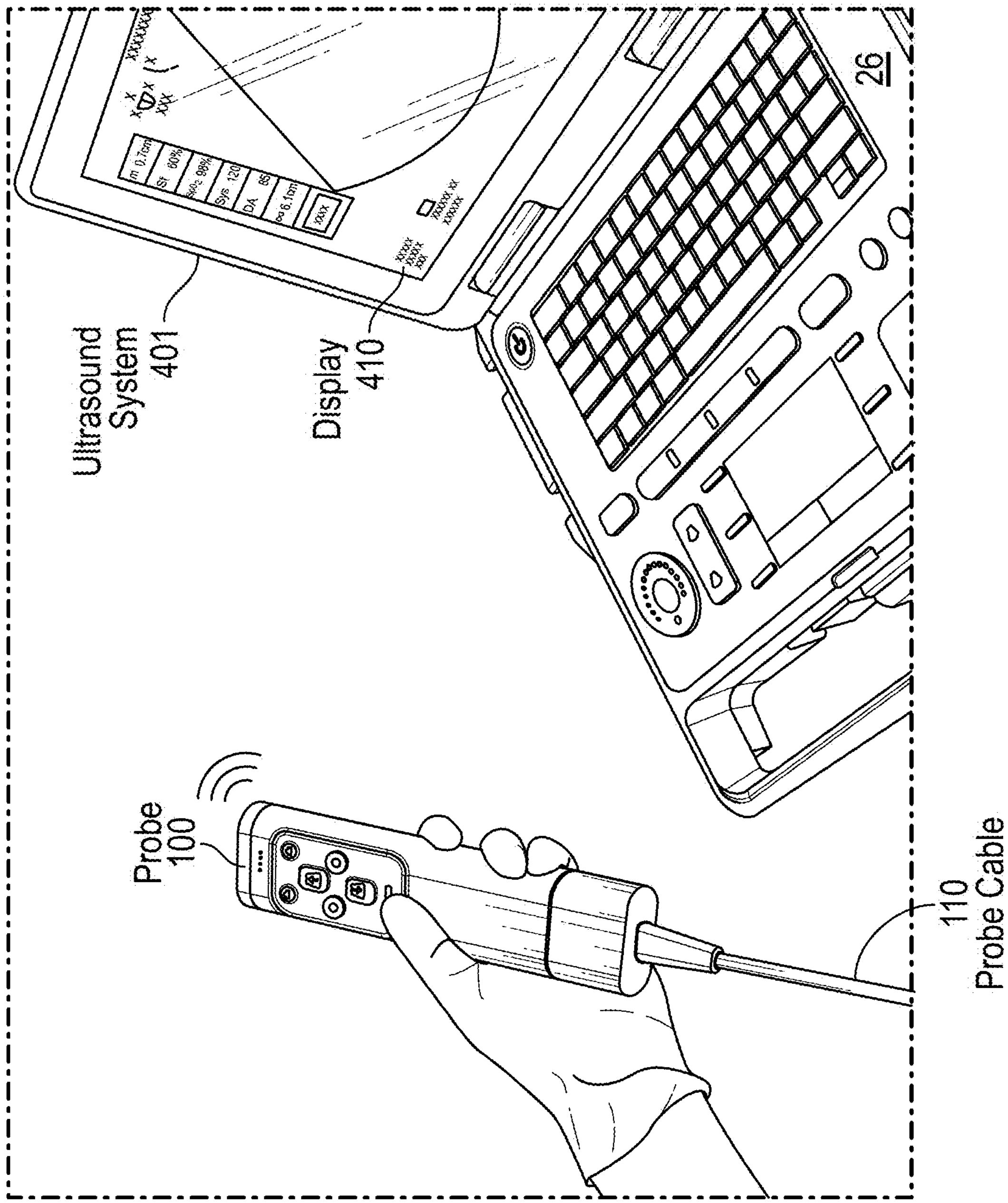
FIG. 4 illustrates one embodiment of an ultrasound system with a probe having TEE and imaging controls.

FIG. 4 illustrates one embodiment of an ultrasound system with a probe having TEE and imaging controls as described above. Referring to FIG. 4, probe 100 has a probe tip coupled to probe cable 110. Ultrasound data corresponding to ultrasound echoes captured by probe 100 are relayed to ultrasound system 401 via a wireless connection using a transceiver in probe 100. That is, ultrasound data is sent to ultrasound system 401 using wireless communication. Ultrasound system 401 includes a transceiver to receive ultrasound data sent by probe 100. In some embodiments, wireless communication between probe 100 and ultrasound system 401 is performed using short-range wireless communication (e.g., Bluetooth, Zigbee, etc.). In response to receiving the ultrasound data, ultrasound system 401 generates ultrasound images that can be displayed on display 410.

In one embodiment, the ultrasound machine has a user interface configured to display an ultrasound image based on the ultrasound data on a display screen. In one embodiment, the user interface is configured to also display a graphical representation of a touch interface of the control panel of the probe on the display screen as well. In some embodiments, the control panel is illustrated as part of the display screen of the ultrasound system to provide the user feedback as to the controls that are being used or exercised on the probe. In some embodiments, the graphic representation of the touch interface (e.g., first indicators for transducer control and second indicators for controlling imaging parameters) is displayed with indications of the finger locations that are proximate to the touch interface and sensed by capacitive sensors in the touch interface of the probe.

In some embodiments, a user interface is configured to display an indicator of the angle that the probe transducer has moved relative to probe cable. In some embodiments, the indicator of the angle of the probe transducer is an indicator of the flexion angle corresponding to the anteflexion and retroflexion movement of the probe transducer and is used to communicate the current flexion state (flex versus straight/unflex) to a user. In some embodiments, the angle indicator indicates the omniplane angle. In one embodiment, the indicator of the angle includes a graphic icon of the tip of the probe transducer and a portion of the probe cable. The graphic enables the user to be able to avoid a dangerous situation by attempting to remove the probe when the probe tip is in a flexed state, which could injure the patient.

In some embodiments, the user interface is configured to display a graphic representing viewpoints and is able to receive a user selection of the viewpoint represented by the graphic. In such a case, in some embodiments, the ultrasound probe is implemented to configure the probe transducer to transmit ultrasound signals based on the viewpoint that is selected.

Figure 5A:
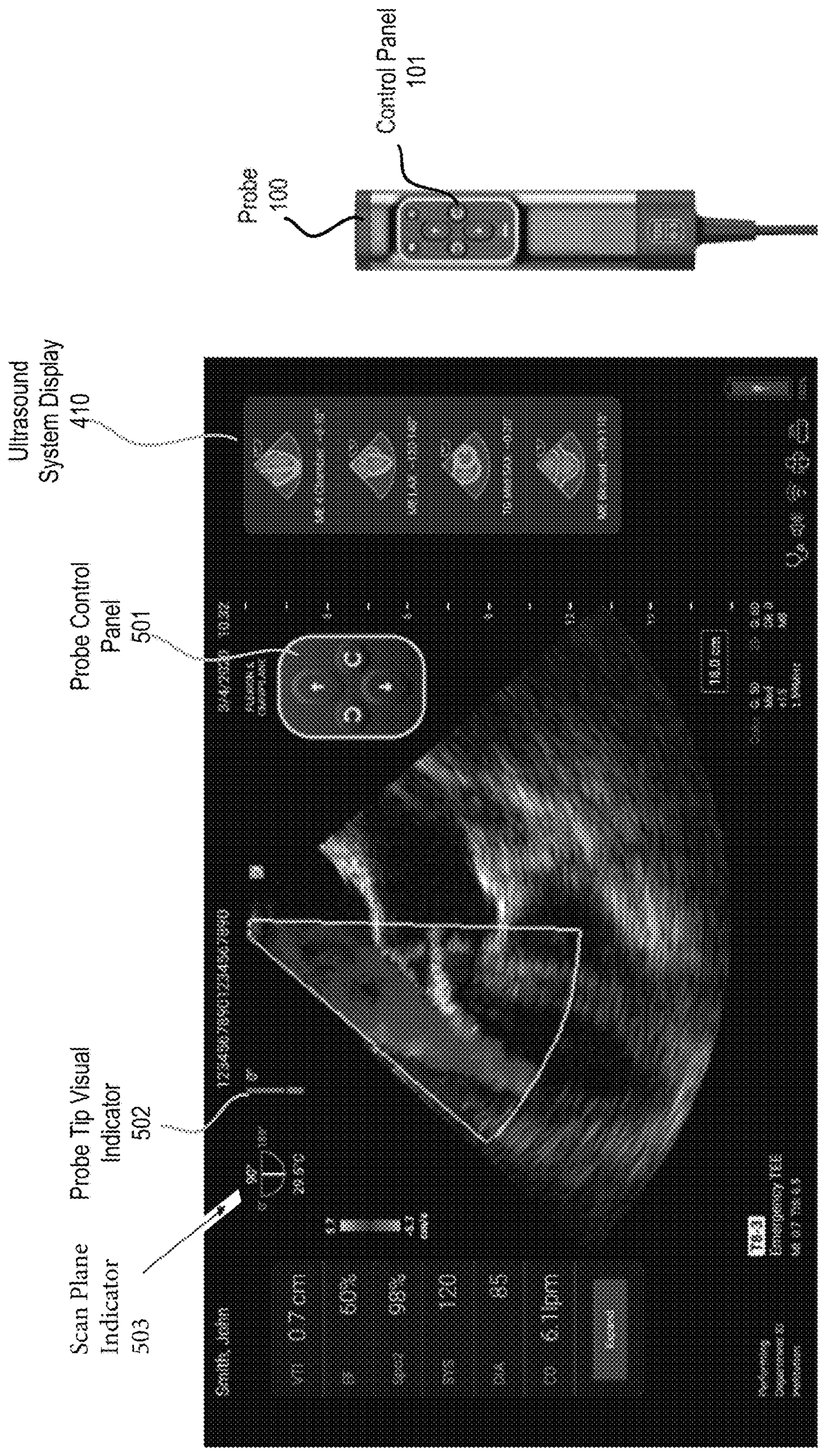
FIGS. 5A-5C illustrate example embodiments of the ultrasound display screen.
Figure 5B:
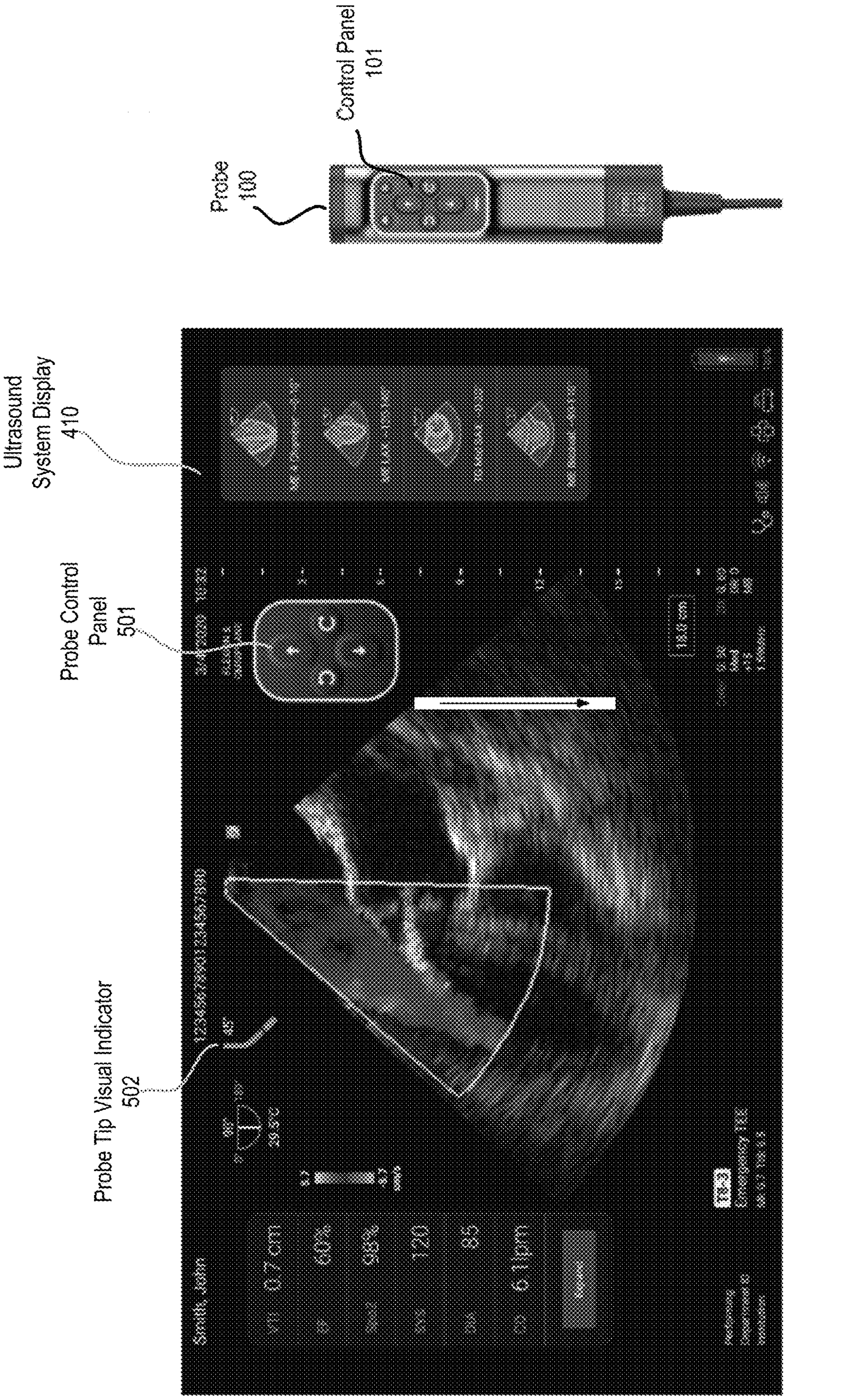
Figure 5C:
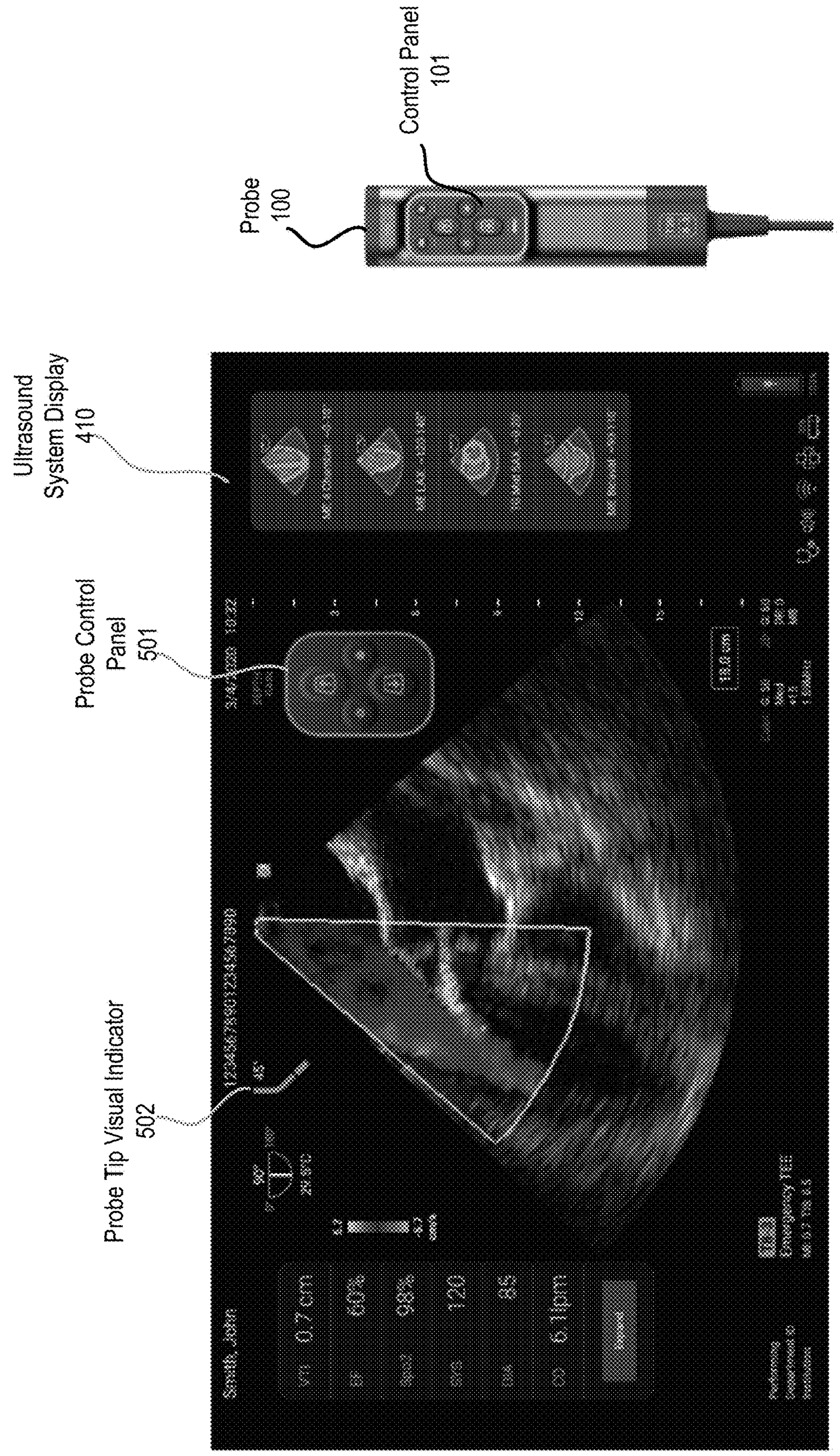

FIGS. 5A-5C illustrate example embodiments of the ultrasound display screen. Referring to FIG. 5A, control panel 101 of probe 100 is illustrated on ultrasound system display 410 as probe control panel 501. In some embodiment, as each button is pressed on control panel 101, the corresponding control button on probe control panel 501 is illuminated on the ultrasound system display 410.

FIG. 5A also illustrates a probe tip visual indicator 502, which illustrates the current orientation of the probe tip. In some embodiments, probe tip visual indicator 502 is an indicator of the flexion angle corresponding to the anteflexion and retroflexion movement of the probe transducer and is used to communicate the current flexion state (flex versus straight/unflex). As illustrated, probe tip visual indicator 502 indicates the probe tip is straight in FIG. 5A. In some embodiments, scan plane indicator 503 indicates the scan plane. In this case, scan plane indicator 503 illustrates that the scan plan is at a 29.5-degree angle. FIG. 5B illustrates another display on the ultrasound image system. In this case, probe tip visual indicator 502 illustrates that the probe tip is at a 45-degree angle. This feedback of the state of the probe tip provides enables the operator to make decisions with respect to the probe based on the probe tip orientation. For example, if the operator wished to extract the probe tip from within a patient, the operator would know that the probe tip being at a 45-degree angle is dangerous for extraction and could press the reset button on the control panel to reset the probe to a limped (e.g., neutral) or non-angled position to allow safe extraction of the probe tip.

FIG. 5C illustrates the ultrasound system display showing the control panel interface for controlling ultrasound imaging that is displayed in response to the user activating the mode switch button on control panel 101. Referring to FIG. 5C, probe control panel 501 shows the gain and depth controls that the operator of the probe has at their disposal in response to pressing the mode switch button.

In one embodiment, the user interface is configured to display one or more graphics representing flexion angles of the transducer for imaging different anatomies. In such a case, the user interface receives a user selection of an additional graphic of the one or more graphics and the ultrasound probe is configured to move, responsive to the user selection of the transducer to a position corresponding to the flexion angle represented by the additional graphic.

In one embodiment, the probe body may be disconnected from the probe end that has the probe cable and its associated probe transducer. The probe body may be disconnected from the probe end while the probe transducer and a portion of the probe cable remain transesophageally inserted into a patient. The use of detachable probes is important in that it allows the probe end to left in a patient and the remainder of the probe may be used with another tip for another patient. In this manner, the extraction of the probe tip from a patient is avoided, potentially saving harm on the patient that may occur through the removal process and/or through a reinsertion process if the probe tip must be reinserted into the patient at a later time.

Once disconnected, the probe body may be detachably connected to another probe end that has an additional transducer that is of a different form factor than the transducer. This enables many different probe ends with different form factors to be connected to the probe body. That is, the different probe ends may have transducers and/or heads that have different sizes and may have probe cables of different lengths. The different form factors may be based on one or more of patient size, patient age and/or patient gender. Thus, by a having a detachable probe end, different probe tips of different sizes may be used for different patients and/or different reasons.

Figure 6A:
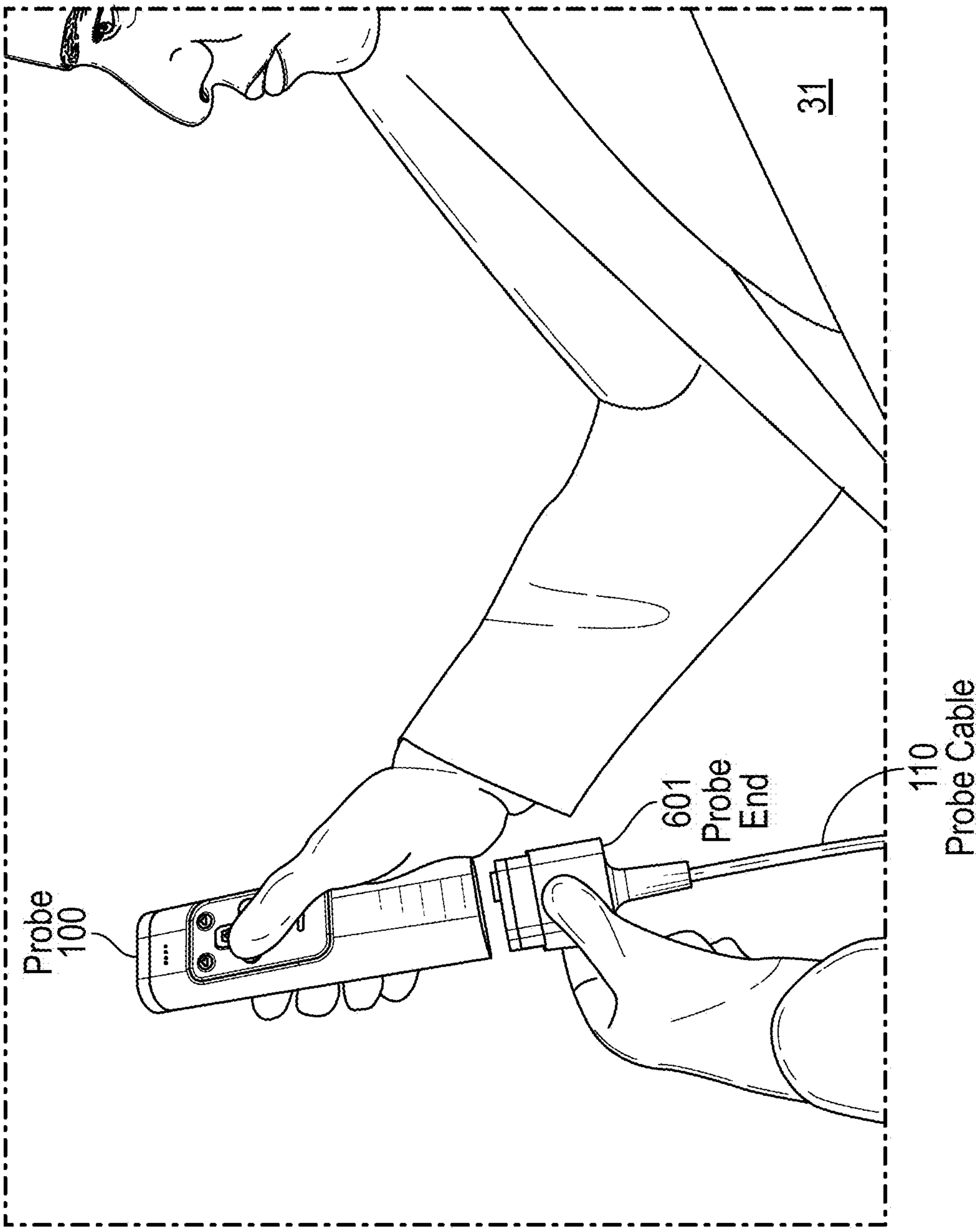
FIG. 6A illustrates some embodiments of a probe with a detachable probe end.

FIG. 6A illustrates some embodiments of a probe with a detachable probe end. Referring to FIG. 6A, probe 100 includes probe end 601 that includes probe cable 110 that is detachable or otherwise removable. In some embodiments, probe end 601 is detached by pressing a button that releases a latch on probe end 601. Other detachments mechanisms can be used. In alternative embodiments, instead of a button, a press fit connection exits between probe end 601 and probe cable 110 and the two can be detached by pulling the two apart. Other connection mechanisms can be used such as, for example, a friction fit, a latch, etc.

Figure 6B:
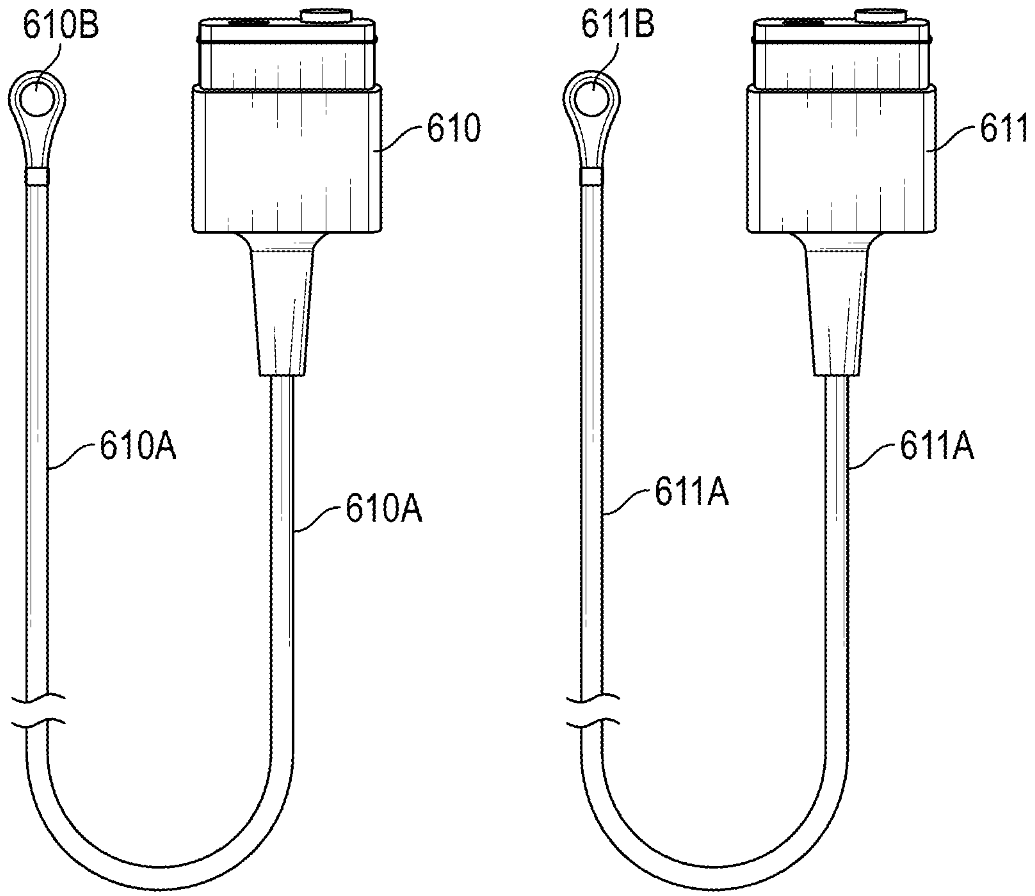
FIG. 6B illustrates examples of different probe ends with different sized probe tips.

FIG. 6B illustrates examples of different probe ends with different sized probe tips. Referring to FIG. 6B, probe end 610 includes probe cable 610A and probe tip 610B, while probe end 611 includes probe cable 611A and probe tip 611B. Note that probe tip 611B is larger than probe tip 610B. In some embodiments, the probe cables, such as probe cables 610A and 611A, can have different diameters and/or probe ends, such as probe ends 610 and 611, having different sizes and/or shapes.

In some embodiments, the ultrasound system includes a mount configured to hold and prevent movement of a proximal probe end of the probe cable when the probe body is disconnected from the probe cable. As mentioned, using this mount, the probe cable and the transducer may remain transesophageally inserted into a patient while probe body is disconnected from the probe cable. In one embodiment, the mount includes a clamp configured to secure the mount to a patient bed or other fixture.

Figure 7:
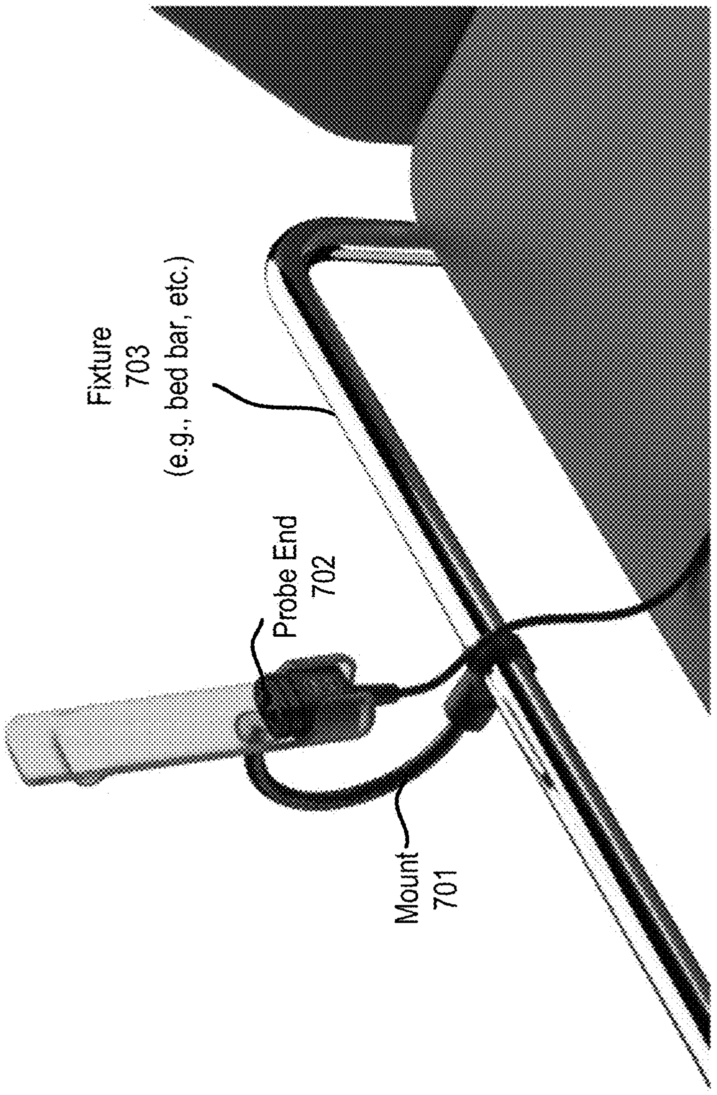
FIG. 7 illustrates some embodiments of a mount to hold a proximal end of the probe cable.

FIG. 7 illustrates one embodiment of a mount to hold a proximal end of the probe cable. Referring to FIG. 7, mount 701 holds probe end 702 to a fixture 703. In one embodiment, fixture 703 is a bed post of a patient bed or other piece of furniture upon which the patient lies while a probe cable and its associated probe tip of probe end 702 remains transesophageally inserted into the patient.

In some embodiments, the ultrasound system includes a cabinet that provides a central location to store and easily deploy a TEE based ultrasound system that has multiple detachable probes. In some embodiments, the cabinet includes a first container configured to store one or more probe cables (and associated probe tips) configured to detachably connect to a probe body. In some embodiments, the first container includes one or more ultraviolet (UV) lights to disinfect the probe cables that are being stored in the first container. In some embodiments, the cabinet further includes a second container to store the probe body and one or more batteries configured to power the probe body. In some embodiments, the second container also includes a charging station configured to charge one or more batteries during the storage in the cabinet.

Figure 8A:
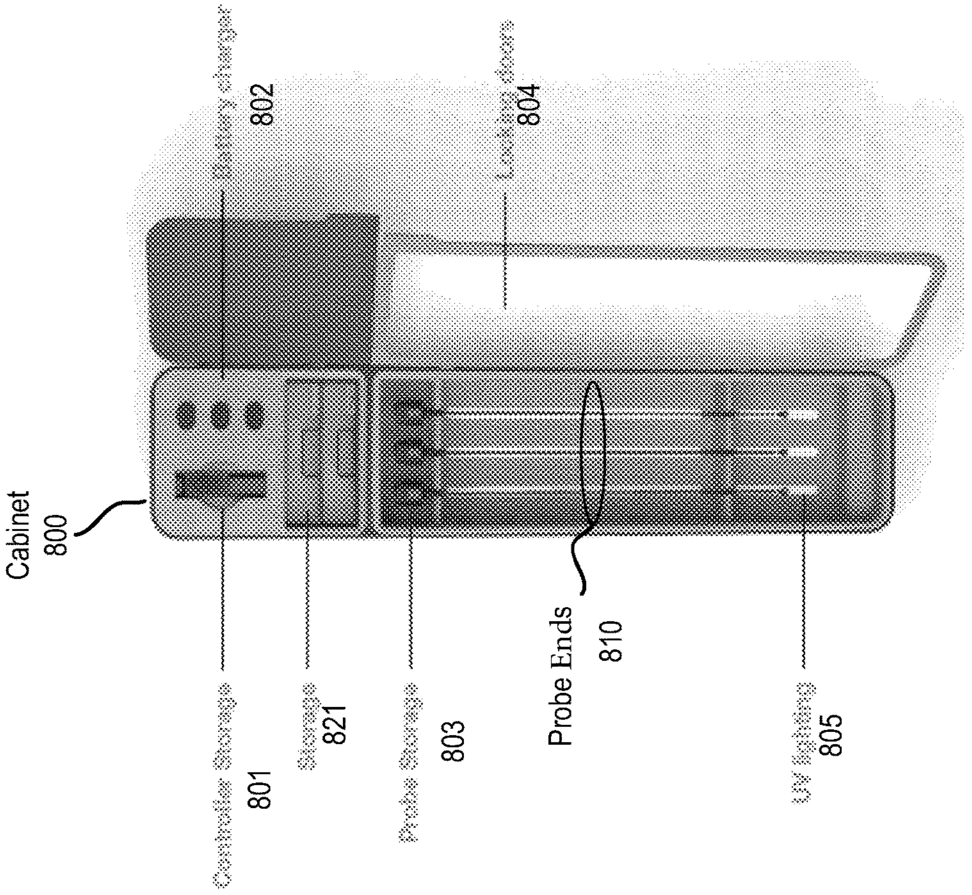
FIG. 8A illustrates some embodiments of a cabinet to store, locate and deploy a probe.

FIG. 8A illustrates some embodiments of a cabinet 800 to store, locate and deploy the probe (e.g., probe 100 of FIG. 1). Referring to FIG. 8A, cabinet 800 includes controller storage 801 to store the upper portion of one or more probes that are detached from the probe ends having the probe cable and their associated probe tips. In some embodiments, cabinet 800 includes battery charger 802 to charge batteries that power the probe.

In some embodiments, cabinet 800 includes probe storage 803 that includes storage for one or more probe ends 810. While three probe ends 810 are shown, cabinet 800 may be designed to store more or less than three probe ends. In some embodiments, ultraviolet lighting 805 is included in a portion of probe storage 803 to allow the probe ends 810 and their associated tips to be illuminated with UV light while in cabinet 800 to facilitate the cleaning and/or disinfecting process.

In some embodiments, cabinet 800 includes doors 804 that may be opened and closed when accessing items in cabinet 800. In some embodiments, doors 804 are locking doors. In some embodiments, cabinet 800 includes additional areas for storage such as, for example, storage 821.

In some embodiments, the cabinet is mounted to a cart to enable movement of the cabinet. In some embodiments, the cart includes a push handle and wheels or other mechanism to facilitate movement of the cart to enable it to be quickly and easily moved around a hospital to ensure the technology is easier deployed when needed. The cart mounted cabinet may also include rear storage and extra exam materials such as wipes, drapes, cleaning supplies and holders, etc.

Figure 8C:
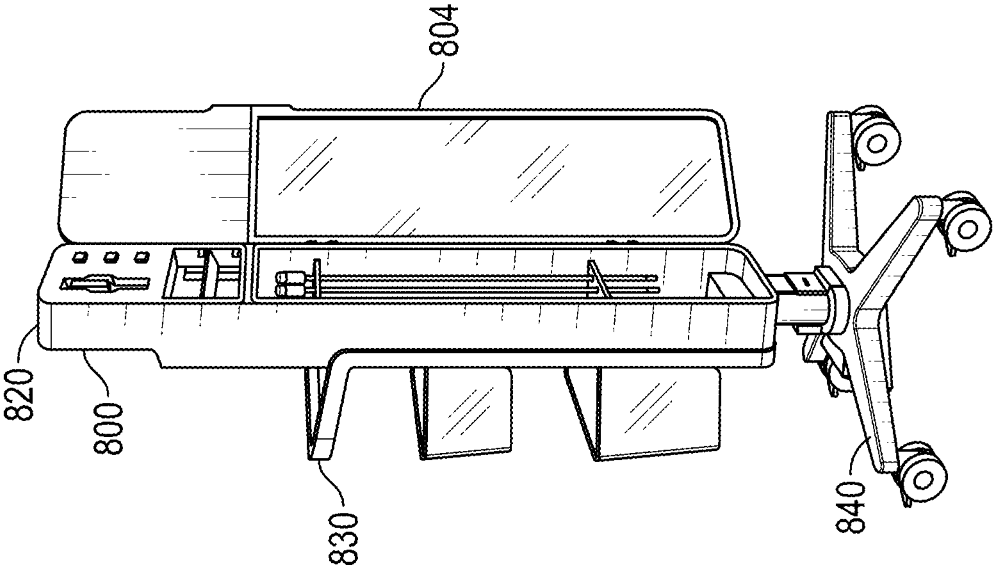
FIGS. 8B and 8C illustrate a cabinet mounted to a cart.
Figure 8B:
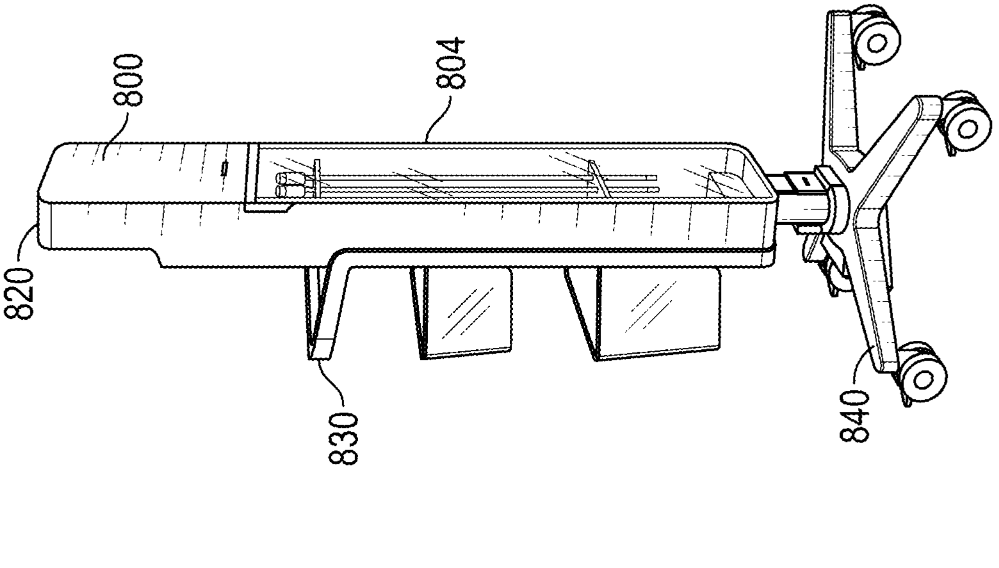

FIGS. 8B and 8C illustrate a cabinet mounted to a cart. Referring to FIGS. 8B and 8C, cart 820 illustrates cabinet 800 mounted to the cart with its locking doors 804 in their closed and opened positions, respectively. As shown in FIGS. 8B and 8C, cart 820 includes a handle 830 and a stand with wheels 840.

In one embodiment, the ultrasound system includes a bite block configured to guard a probe cable from a patient's bite and prevent anteflexion and retroflexion movement of the transducer until a predetermined length of the cable probe is inserted during a transesophageal insertion process with a probe. The predetermined length can be determined by the operator of the ultrasound system so that the cable clears a patient's throat before flexion movement is enabled. In one embodiment, the bite block is configured to activate and deactivate a control of the flexion angle with the control panel of the probe based on an amount the probe cable that is transesophageally inserted through the bite block. In other words, one or more functions (e.g., buttons) of the control panel interface on the probe are enabled or disabled during at least a portion of the transesophageal insertion process based on the amount of probe cable that has been inserted into the patient.

In some embodiments, the bite block is implemented to determine an amount of the probe cable that the probe cable is transesophageally inserted during a transesophageal insertion, and deactivates the control of the probe's transducer with a control panel interface (e.g., the touch interface) based on the amount of the probe cable that has been transesophageally inserted. In some embodiments, the probe cable includes markers to visually indicate the amount the probe cable is transesophageally inserted. In some embodiments, the bite block includes a sensor that generates a trigger signal when the probe cable is inserted to a predetermined length into a patient and a transceiver implemented to communicate the trigger signal through the probe body. In some embodiments, the probe body, upon receipt of the trigger signal via a transceiver in the probe body, is configured to control the anteflexion and retroflexion movement of the transducer. In some embodiments, the transceivers of the bite block and the probe body performs communication using a short-range wireless communication (e.g., Bluetooth, Zigbee, etc.). In some embodiments, the transceiver of the probe body is the same transceiver used to communicate with the ultrasound system.

In some embodiments, the bite block is implemented to prevent the anteflexion and retroflexion movement of a probe's transducer during a transesophageal removal of the probe cable. In some embodiments, the anteflexion and retroflexion movement of the transducer is prevented by configuring the probe's transducer into a limp state until a predetermined length of the probe cable is removed from the patient. For instance, the predetermined length can be chosen so that enough of the cable is removed from a patient to clear a particular anatomy, such as the throat or larynx. Additionally or alternatively, the predetermined length can be based on the length of the cable that was inserted into the patient, such as 50%, 75%, or 100% of the length of the cable inserted into the patient. In an example, the predetermined length is based on the distance the cable is inserted into the patient. For instance, the cable may need to be clear of the bite block, or close to clear of the bite block until the limp state is disabled. In such a case, the bite block uses a sensor to determine that the probe cable is being removed (e.g., starting to be removed from the patient) and uses a transceiver to communicate information indicative of the probe cable removal. In response to receiving the information via a transceiver in the probe body, the probe body configures the probe's transducer into a limp state (e.g., a reset state) until the predetermined length of the probe cable is removed from the patient.

In some embodiments, the bite block includes a locking mechanism configured to lock the probe cable and prevent positional drift of the transducer. The locking mechanism (e.g., a cam) can clamp the probe cable to the bite block, such as with a mechanical lock and/or electromagnetic lock. In an example, the locking mechanism is implemented to apply additional friction to inhibit the cable from moving through the bite block.

Figure 9:
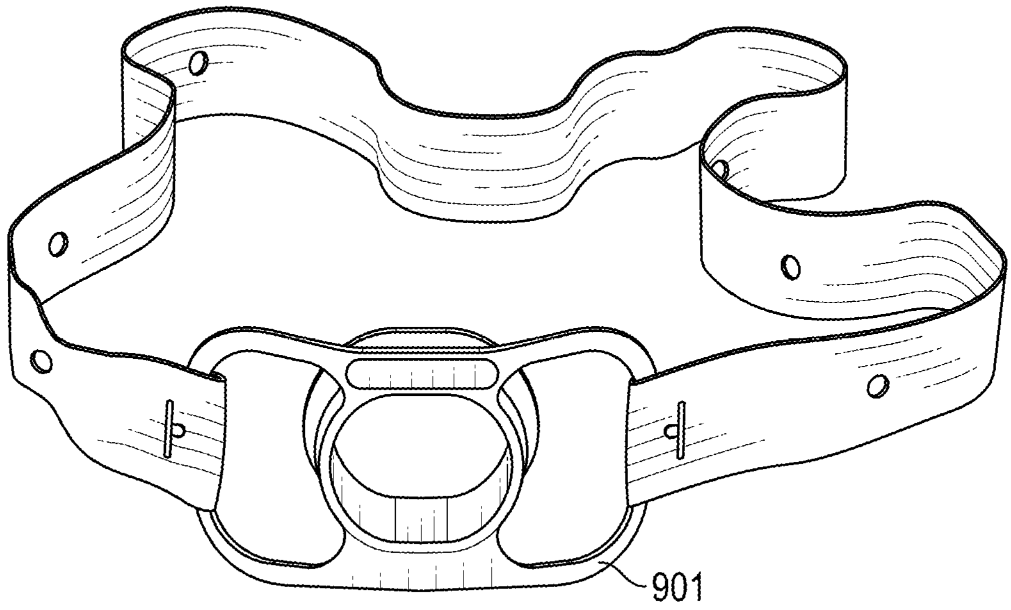
FIG. 9 illustrates one embodiment of a bite block.
Figure 9A:
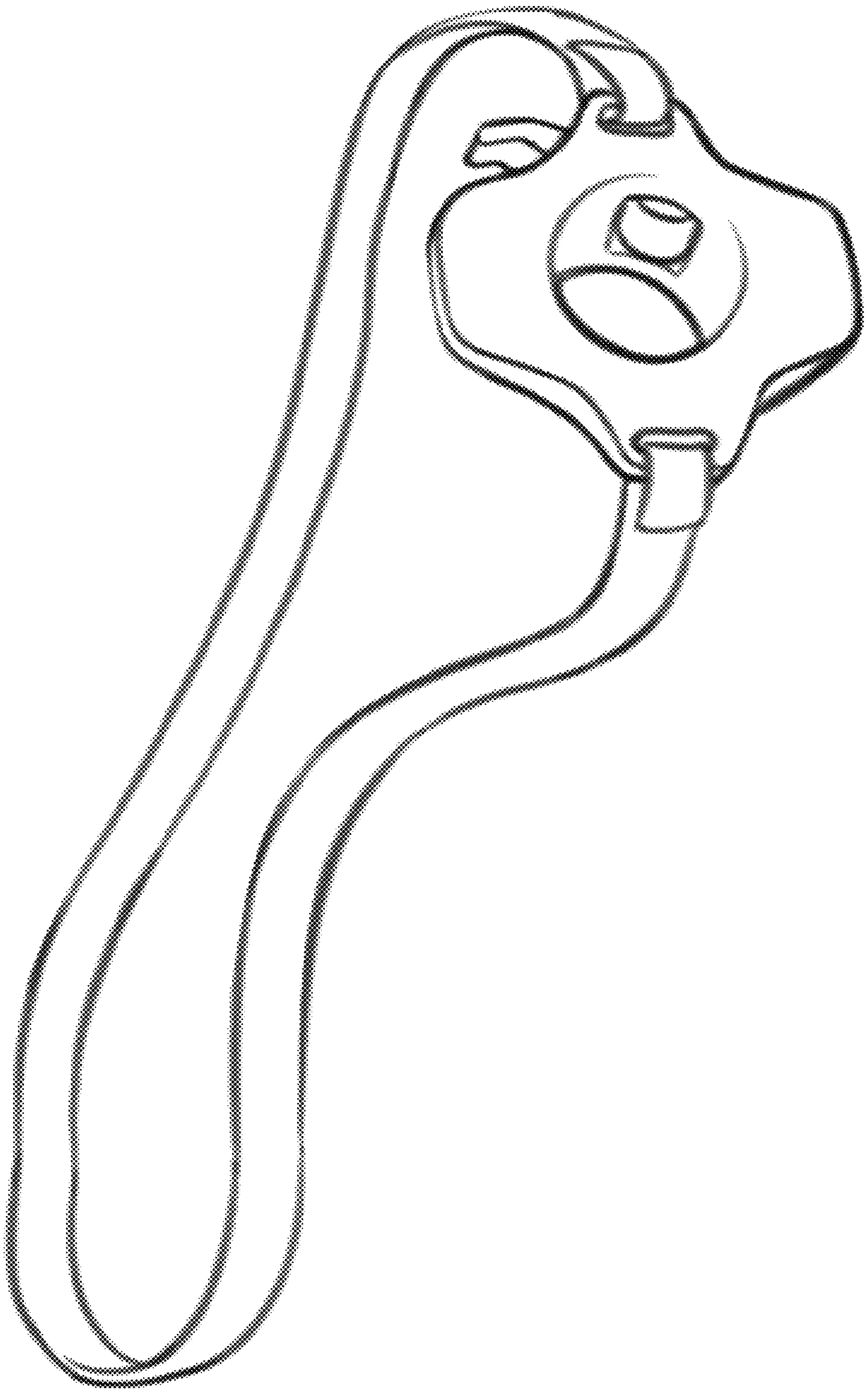
FIG. 9A illustrates another embodiment of a bite block.

FIG. 9 illustrates one embodiment of a bite block 901. FIG. 9A illustrates another embodiment of a bite block.

Example of an Ultrasound Imaging System

In some embodiments, the ultrasound machine includes an ultrasound imaging system includes ultrasound system electronics that comprises one or more processors, integrated circuits, application-specific integrated circuits (ASICs), field programmable gate arrays (FPGAs), and power sources to support the functioning of the ultrasound imaging system in a manner well-known in the art. In some embodiments, the ultrasound imaging system also includes an ultrasound control subsystem having one or more processors. One or more processors process the ultrasound data received from the probe and form an image that is sent to the ultrasound imaging subsystem, which displays the image on a display screen (e.g., display screen 410 of FIG. 4). Thus, the display screen displays ultrasound images from the ultrasound data processed by the processor of the ultrasound control subsystem.

In some embodiments, the ultrasound system also has one or more user input devices (e.g., a keyboard, a cursor control device, etc.) that inputs data and allows the taking of measurements from the display of the ultrasound display subsystem, a disk storage device (e.g., hard, floppy, thumb drive, compact disks (CD), digital video discs (DVDs)) for storing the acquired images, and a printer that prints the image from the displayed data. These also have not been shown to avoid obscuring the techniques disclosed herein.

In some embodiments, the ultrasound image machine includes a neural network configured to generate image quality measures. The image quality measures may correspond to a range of angles offset from a viewpoint used to capture the ultrasound image. In such case, in some embodiments, the ultrasound machine is configured to change the viewpoint based on the image quality measures. In some embodiments, an imaging processing algorithm is used to anticipate a suitable angle for each view desired.

In some embodiments, the neural network is configured to generate a target flexion angle based on an ultrasound image and a flexion angle represented by an additional graphic of one or more graphics received from a user selection of the user interface. In such a case, the ultrasound probe is configured to move the transducer to a position of a corresponding position to the target flexion angle. In some embodiments, the graphic supplied on the screen by which the artificial intelligence analysis automatically adjusts the omniplane angle to an ideal angle in order to achieve a suitable view.

Figure 10:
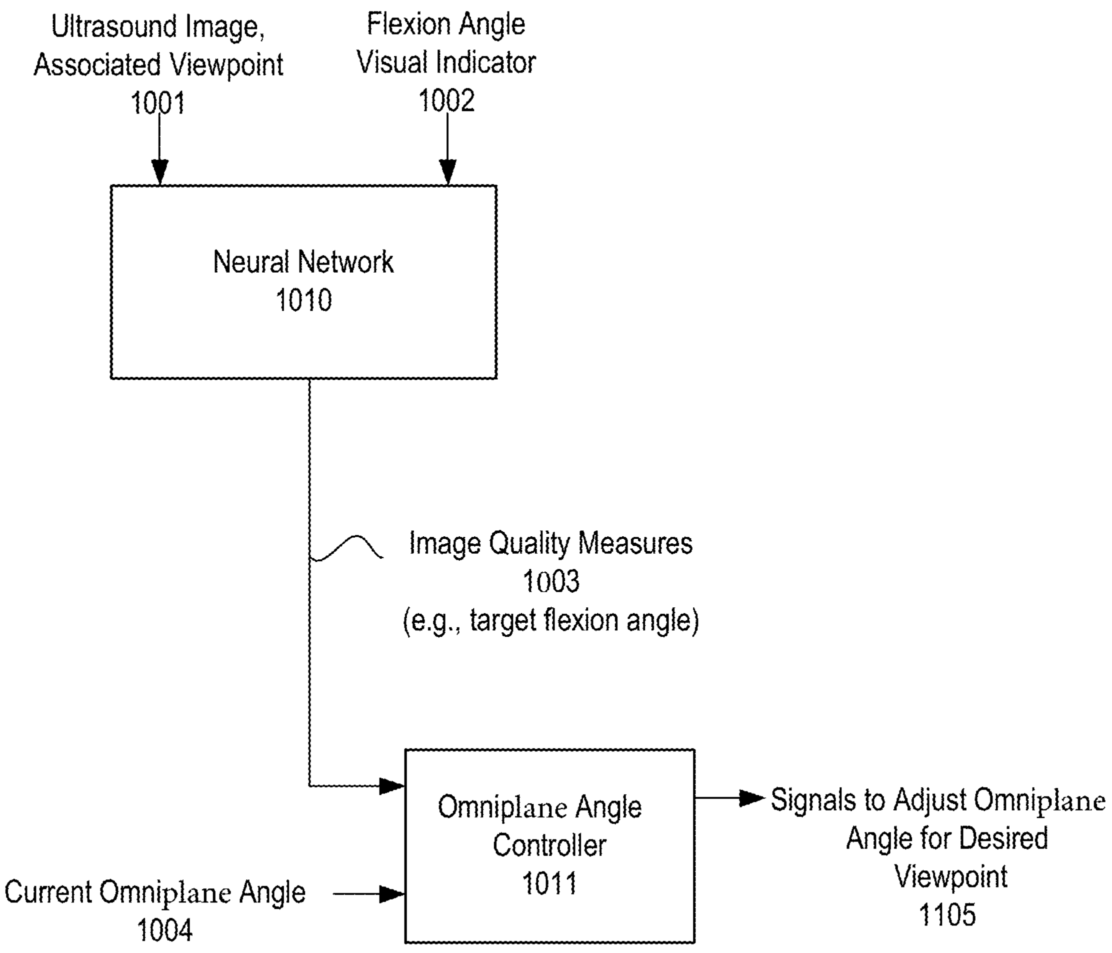
FIG. 10 is one embodiment of a neural network of an ultrasound system.

FIG. 10 illustrates some embodiments of a neural network of an ultrasound system. Referring to FIG. 10, neural network 1010 receives ultrasound data 1001 with its associated viewpoint information along with a flexion angle visual indicator 1002. Based on these inputs, neural network 1010 generates image quality measures 1003. In some embodiments, image quality measures 1003 comprise a target flexion angle.

In some embodiment, image quality measures 1003 (e.g., a target flexion angle) and a current omniplane angle 1004 are input to an omnipresent angle controller 1011. In response to these inputs, omniplane angle controller 1011 generates signals 1105 to adjust the omniplane angle to obtain the desired (e.g., optimal) viewpoint. The signals are fed back to the probe to cause the probe to move its transducer to obtain ultrasound data that may be used by the ultrasound imaging system to generate and display an ultrasound image with the desired viewpoint.

Example Flow Diagrams

Figure 11:
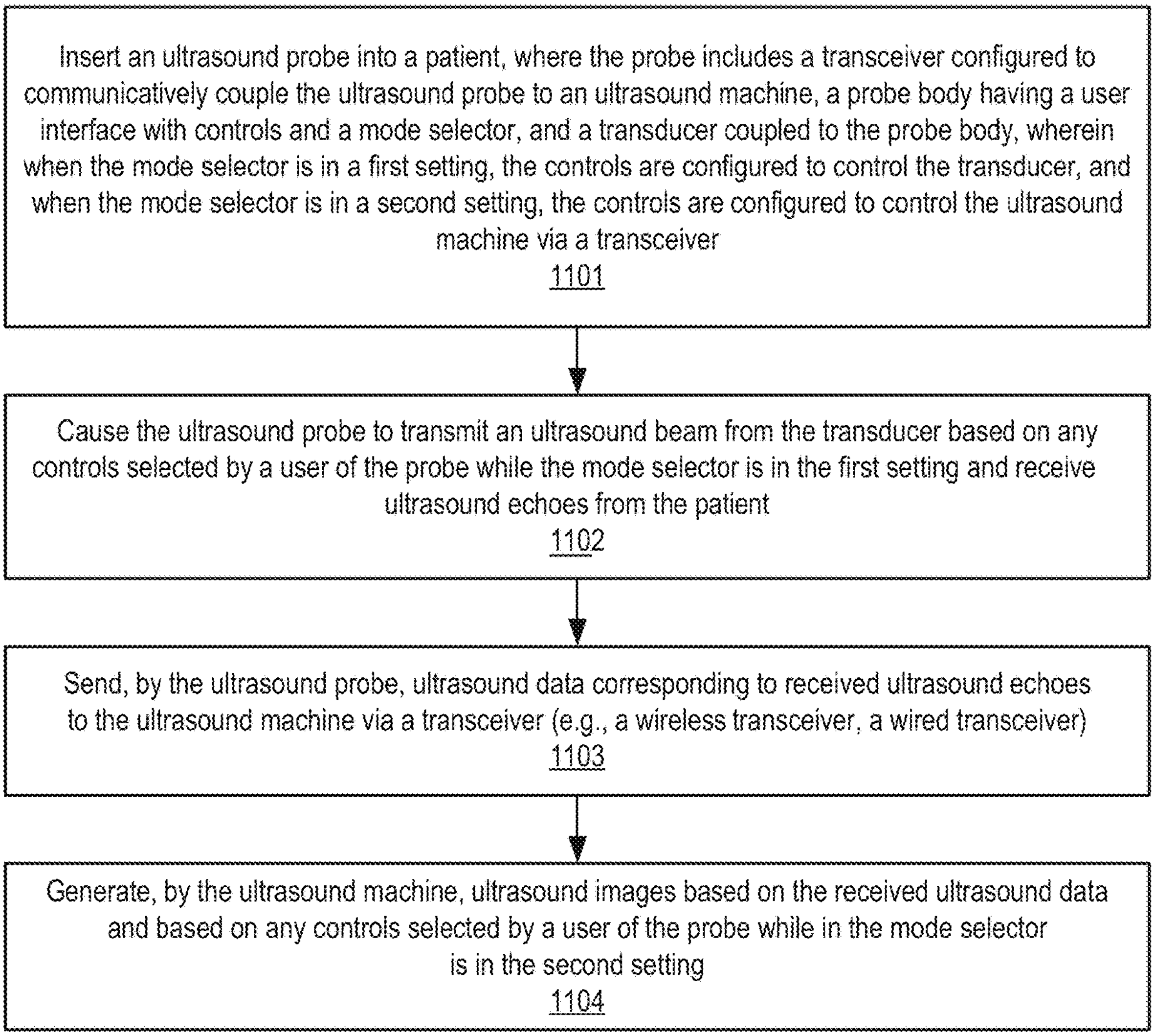
FIG. 11 is a data flow diagram of some embodiments of process for performing an ultrasound examination.

FIG. 11 illustrates a data flow diagram of some embodiments of a process for performing an ultrasound examination. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound system with an ultrasound machine and an ultrasound probe, such as, for example, described above.

Referring to FIG. 11, the process begins by processing logic inserting an ultrasound probe into a patient, where the probe includes a transceiver configured to communicatively couple the ultrasound probe to an ultrasound machine, a probe body having a user interface with controls and a mode selector, and a transducer coupled to the probe body, wherein when the mode selector is in a first setting, the controls are configured to control the transducer, and when the mode selector is in a second setting, the controls are configured to control the ultrasound machine with controls sent via a transceiver within the probe (processing block 1101).

In some embodiments, the controls include one or more first controls and one or more second controls configured to control depth and gain of the ultrasound machine, respectively, when the mode selector is in the second setting. In some embodiments, when the mode selector is in the first setting, the one or more first controls are configured to control anteflexion and retroflexion movement of the transducer. In some embodiments, when the mode selector is in the first setting, the one or more second controls are configured to control omniplane left and omniplane right ultrasound transmission of the transducer. In some embodiments, when the mode selector is in the second setting, the user interface is configured to illuminate a portion of the user interface to indicate the control of depth and gain of the ultrasound machine.

In some embodiments, the transducer includes a transducer cable implemented to couple the transducer to the probe body, and the controls include a reset selector configured to, when activated, mechanically return the transducer to a default angle relative to the transducer cable. In some embodiments, the transducer cable is configured for esophageal insertion.

In some embodiments, the probe body is implemented to disconnect from the transducer and detachably connect to an additional transducer that is of a different form factor than the transducer. In some embodiments, the different form factor is based on one or more of a patient size, a patient age, and a patient gender. In some embodiments, the additional transducer is of the different form factor by including an additional transducer cable that is a different length than a transducer cable of the transducer, the additional transducer cable configured to couple the additional transducer to the probe body.

Processing logic causes the ultrasound probe to transmit an ultrasound beam from the transducer based on any controls selected by a user of the probe while the mode selector is in the first setting and receive ultrasound echoes from the patient (processing block 1102). In some embodiments, the transceiver of the probe is configured to implement a wireless communication link to communicatively couple the ultrasound probe to the ultrasound machine.

Then processing logic sends ultrasound data corresponding to received ultrasound echoes to the ultrasound machine via the transceiver (e.g., a wireless transceiver, a wired transceiver, or combinations thereof) (processing block 1103).

Thereafter, processing logic of the ultrasound machine generates ultrasound images based on the received ultrasound data and based on any controls selected by a user of the probe while in the mode selector is in the second setting (processing block 1104).

Figure 12:
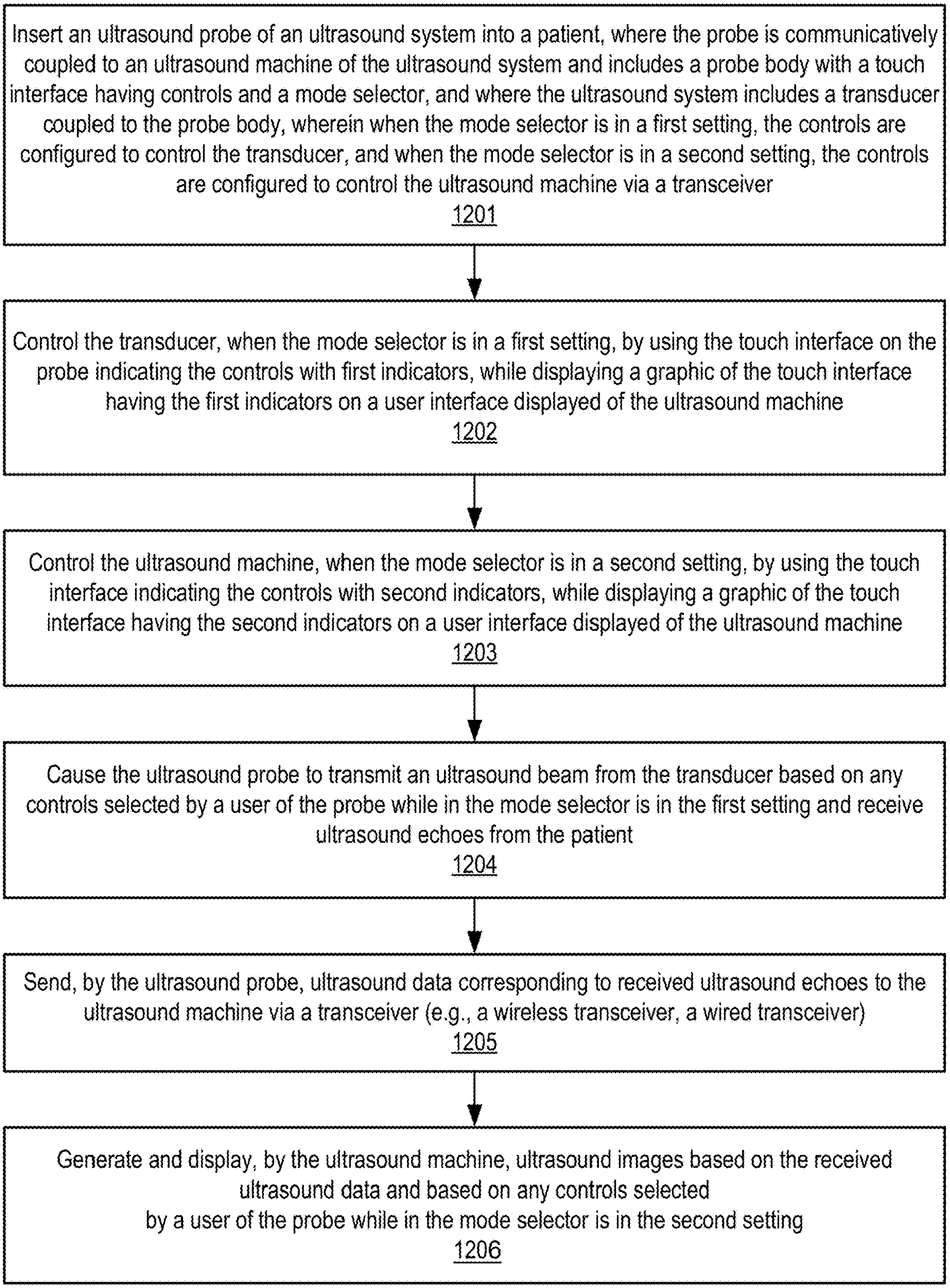
FIG. 12 is a data flow diagram of some embodiments of process for performing an ultrasound examination.

FIG. 12 illustrates a data flow diagram of some embodiments of process for performing an ultrasound examination. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound system with an ultrasound machine and an ultrasound probe, such as, for example, described above.

Referring to FIG. 12, the process begins by processing logic inserting an ultrasound probe of an ultrasound system into a patient, where the probe is communicatively coupled to an ultrasound machine of the ultrasound system and includes a probe body with a touch interface having controls and a mode selector, and where the ultrasound system includes a transducer coupled to the probe body (processing block 1201). In some embodiments, when the mode selector is in a first setting, the controls are configured to control the transducer, and when the mode selector is in a second setting, the controls are configured to control the ultrasound machine via a transceiver in the probe. In some embodiments, the controls include one or more first controls and one or more second controls configured to control depth and gain of the ultrasound machine, respectively, when the mode selector is in the second setting and, when the mode selector is in the first setting, the one or more first controls are configured to control anteflexion and retroflexion movement of the transducer and the one or more second controls are configured to control omniplane left and omniplane right ultrasound transmission of the transducer.

In some embodiments, the controls are configured to control an omniplane angle of ultrasound transmitted by the transducer, and the user interface is configured to display an indicator of the omniplane angle.

In some embodiments, the user interface is configured to display one or more graphics representing flexion angles of the transducer for imaging different anatomies and receive a user selection of an additional graphic of the one or more graphics, and the ultrasound probe is configured to move, responsive to the user selection, the transducer to a position corresponding to a flexion angle represented by the additional graphic.

In some embodiments, the transducer includes a transducer cable implemented to couple the transducer to the probe body, a tip of the transducer is configured to move at an angle relative to the transducer cable based on the controls, and the user interface is configured to display an indicator of the angle. In some embodiments, the indicator of the angle includes a graphic icon of the tip of the transducer and a portion of the transducer cable.

Processing logic controlling the transducer, when the mode selector is in a first setting, by using the touch interface to indicate the controls with first indicators, while displaying a graphic of the touch interface having the first indicators on a user interface displayed of the ultrasound machine (processing block 1202).

Processing logic controlling the ultrasound machine, when the mode selector is in a second setting, by using the touch interface to indicate the controls with second indicators, while displaying a graphic of the touch interface having the second indicators on a user interface displayed of the ultrasound machine (processing block 1203).

Processing logic causes the ultrasound probe to transmit an ultrasound beam from the transducer based on any controls selected by a user of the probe while in the mode selector is in the first setting and receive ultrasound echoes from the patient (processing block 1204).

Then, processing logic sends ultrasound data corresponding to received ultrasound echoes to the ultrasound machine via a transceiver (e.g., a wireless transceiver, a wired transceiver, or combinations thereof) (processing block 1205).

Thereafter, processing logic of the ultrasound machine generates and displays ultrasound images based on the received ultrasound data and based on any controls selected by a user of the probe while in the mode selector is in the second setting (processing block 1206).

Figure 13:
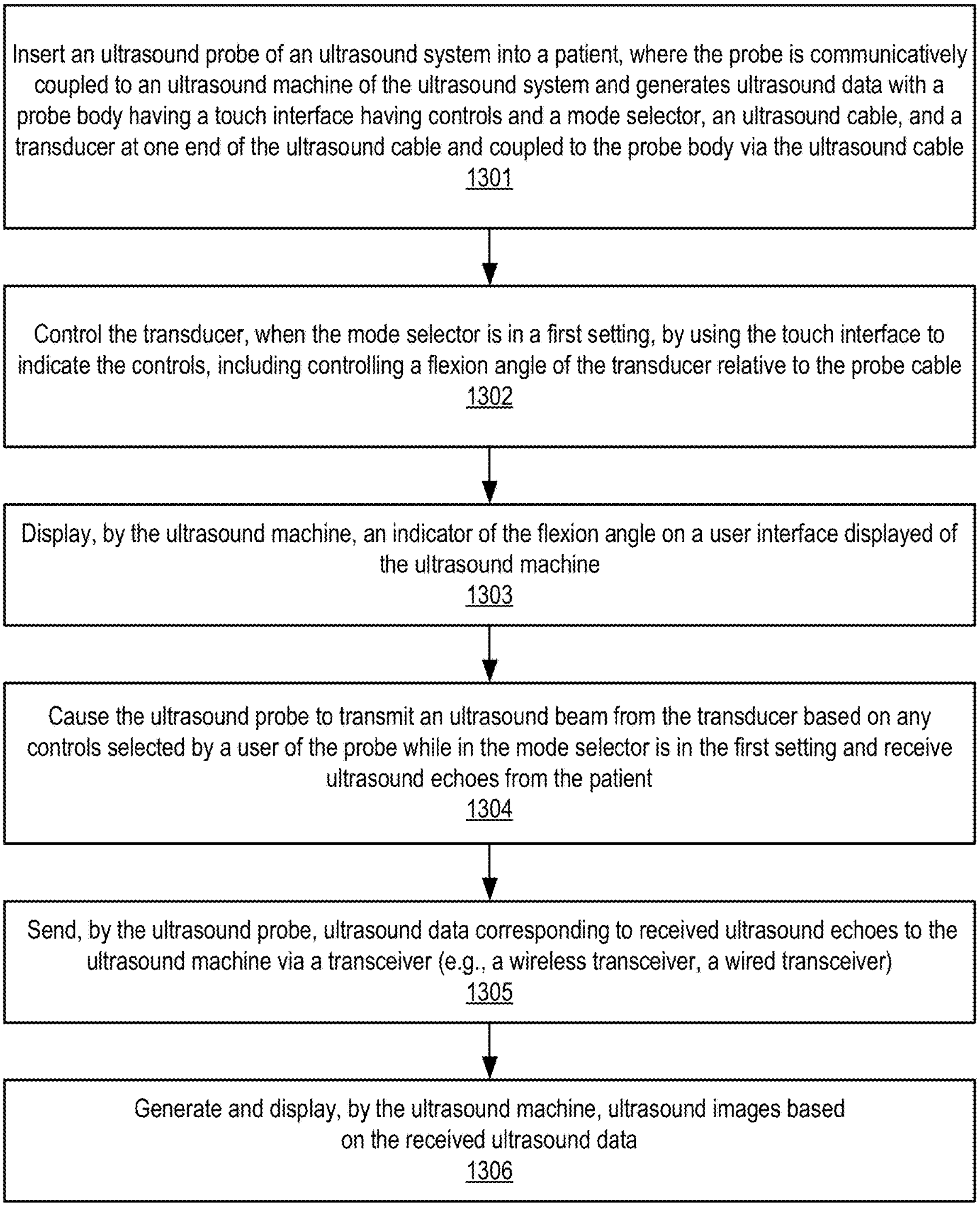
FIG. 13 is a data flow diagram of some embodiments of process for performing an ultrasound examination.

FIG. 13 illustrates a data flow diagram of some embodiments of process for performing an ultrasound examination. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound system with an ultrasound machine and an ultrasound probe, such as, for example, described above.

Referring to FIG. 13, the process begins by processing logic inserting an ultrasound probe of an ultrasound system into a patient, where the probe is communicatively coupled to an ultrasound machine of the ultrasound system and generates ultrasound data with a probe body having touch interface with controls and a mode selector, an ultrasound cable, and a transducer at one end of the ultrasound cable and coupled to the probe body via the ultrasound cable (processing block 1301).

In some embodiments, the user interface is configured to display a graphic representation of the touch interface. In some embodiments, the touch interface includes sensors configured to sense finger locations proximate to the touch interface, and the user interface is configured to display the graphic representation of the touch interface with indications of the finger locations.

In some embodiments, the user interface is configured to display a graphic representing view planes and receive a user selection of a view plane represented by the graphic, and the ultrasound probe is implemented to configure the transducer to transmit ultrasound based on the view plane. In some embodiments, the ultrasound machine includes a neural network configured to generate image quality measures corresponding to a range of angles offset from a view plane used to capture the ultrasound image, and the ultrasound machine is configured to change the view plane based on the image quality measures.

Processing logic controls the transducer, when the mode selector is in a first setting, by using the touch interface to indicate the controls, including controlling a flexion angle of the transducer relative to the probe cable (processing block 1302). In some embodiments, when the mode selector is in a second setting, the controls are configured to control one or more imaging parameters of the ultrasound machine.

Processing logic of the ultrasound machine displays an indicator of the flexion angle on a user interface displayed of the ultrasound machine (processing block 1303). In some embodiments, the user interface is configured to display one or more graphics representing flexion angles of the transducer for imaging different anatomies, and receive a user selection of an additional graphic of the one or more graphics. In some embodiments, the ultrasound machine includes a neural network configured to generate a target flexion angle based on the ultrasound image and an additional flexion angle represented by the additional graphic, and the ultrasound probe is configured to move the transducer to a position corresponding to the target flexion angle.

Processing logic causes the ultrasound probe to transmit an ultrasound beam from the transducer based on any controls selected by a user of the probe while in the mode selector is in the first setting and receive ultrasound echoes from the patient (processing block 1304).

Processing logic of the ultrasound probe sends ultrasound data corresponding to received ultrasound echoes to the ultrasound machine via a transceiver (e.g., a wireless transceiver, a wired transceiver, or combinations thereof) (processing block 1305).

Thereafter, processing logic of the ultrasound machine generates and displays ultrasound images based on the received ultrasound data (processing block 1306).

Figure 14:
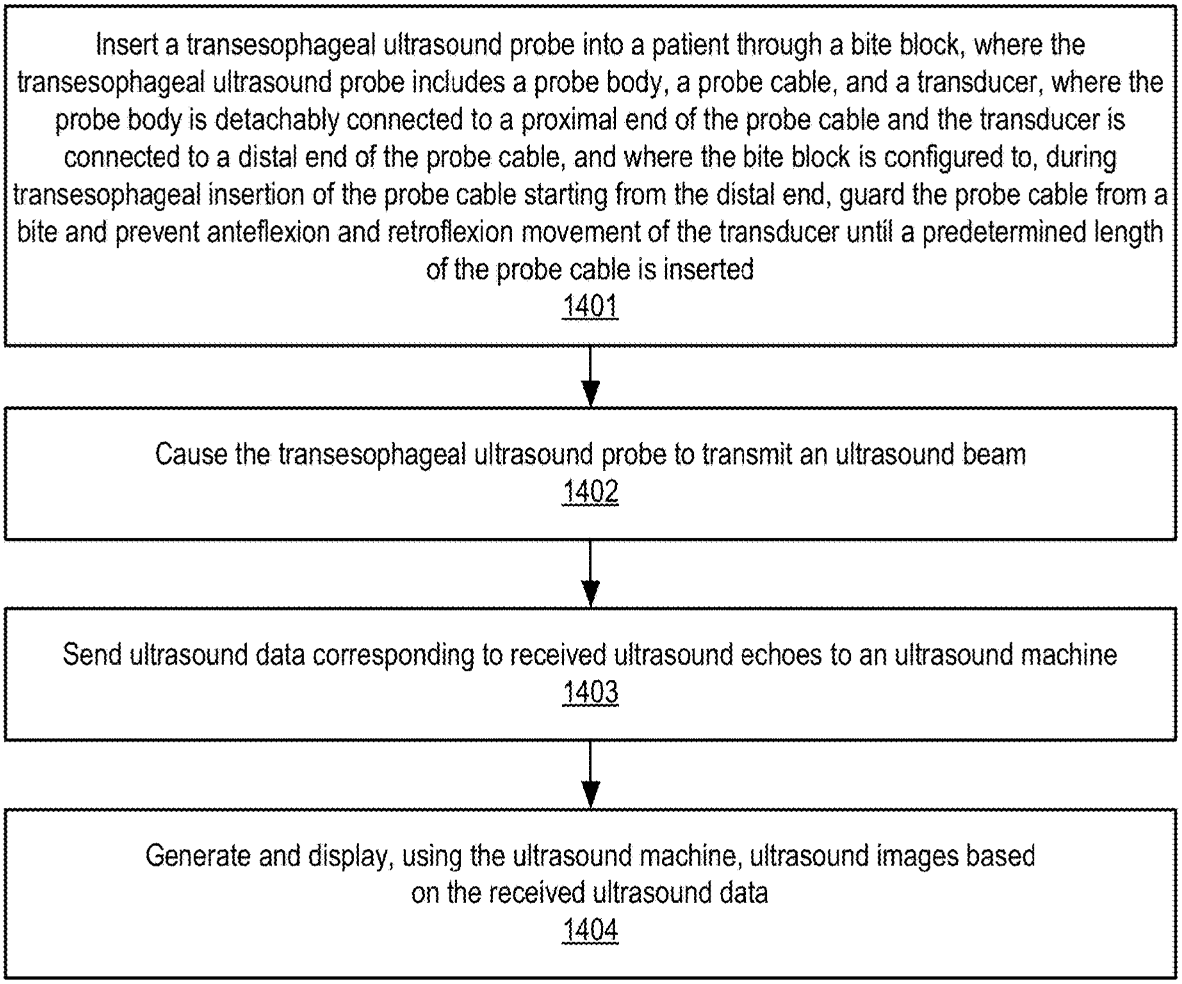
FIG. 14 is a data flow diagram of some embodiments of process for performing an ultrasound examination.

FIG. 14 illustrates a data flow diagram of some embodiments of process for performing an ultrasound examination. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, a transesophageal ultrasound system with an ultrasound machine and an ultrasound probe, such as, for example, described above.

Referring to FIG. 14, the process begins by inserting a transesophageal ultrasound probe into a patient through a bite block, where the transesophageal ultrasound probe includes a probe body, a probe cable, and a transducer, where the probe body is detachably connected to a proximal end of the probe cable and the transducer is connected to a distal end of the probe cable, and where the bite block is configured to, during transesophageal insertion of the probe cable starting from the distal end, guard the probe cable from a bite and prevent anteflexion and retroflexion movement of the transducer until a predetermined length of the probe cable is inserted (processing block 1401).

In some embodiments, the bite block is implemented to, during transesophageal removal of the probe cable, prevent the anteflexion and retroflexion movement of the transducer by configuring the transducer in a limp state until an additional predetermined length of the probe cable is removed. In some embodiments, the bite block includes a sensor implemented to generate a trigger signal when the probe cable is inserted to the predetermined length, and a transceiver implemented to communicate the trigger signal to the probe body, where the probe body, upon receipt of the trigger signal, is configured to control the anteflexion and retroflexion movement of the transducer.

In some embodiments, the probe body is implemented to be disconnected from the probe cable while the transducer and a portion of the probe cable remain transesophageally inserted. In some embodiments, the probe body, once disconnected from the probe cable, is configured to be detachably connected to an additional probe cable. In some embodiments, the additional probe cable is of a different length than the probe cable or is connected to an additional transducer that is of a different diameter or head size than the transducer. In some embodiments, the probe body is implemented to generate haptic feedback that mimics mechanical resistance of a cable mechanism.

In some embodiments, a cabinet includes a first container configured to store the probe cable and additional probe cables configured to detachably connect to the probe body, with the first container including an ultraviolet light source to disinfect the probe cable and the additional probe cables, and a second container configured to store the probe body and one or more batteries configured to power the probe body, the second container including a charging station configured to charge the one or more batteries during storage in the cabinet.

Processing logic causes the transesophageal ultrasound probe to transmit an ultrasound beam (processing block 1402) and sends ultrasound data corresponding to received ultrasound echoes to an ultrasound machine (processing block 1403). In some embodiments, the ultrasound machine is communicatively coupled to the transesophageal ultrasound probe, where the ultrasound machine includes a user interface configured to display an indicator of a flexion angle corresponding to the anteflexion and retroflexion movement of the transducer.

In some embodiments, a hand-worn radiator is configured to be placed on a patient location and control the anteflexion and retroflexion movement of the transducer so that the transducer directs ultrasound in a direction based on the patient location.

Thereafter, processing logic of the ultrasound machine generates and displays ultrasound images based on the received ultrasound data (processing block 1404).

Figure 15:
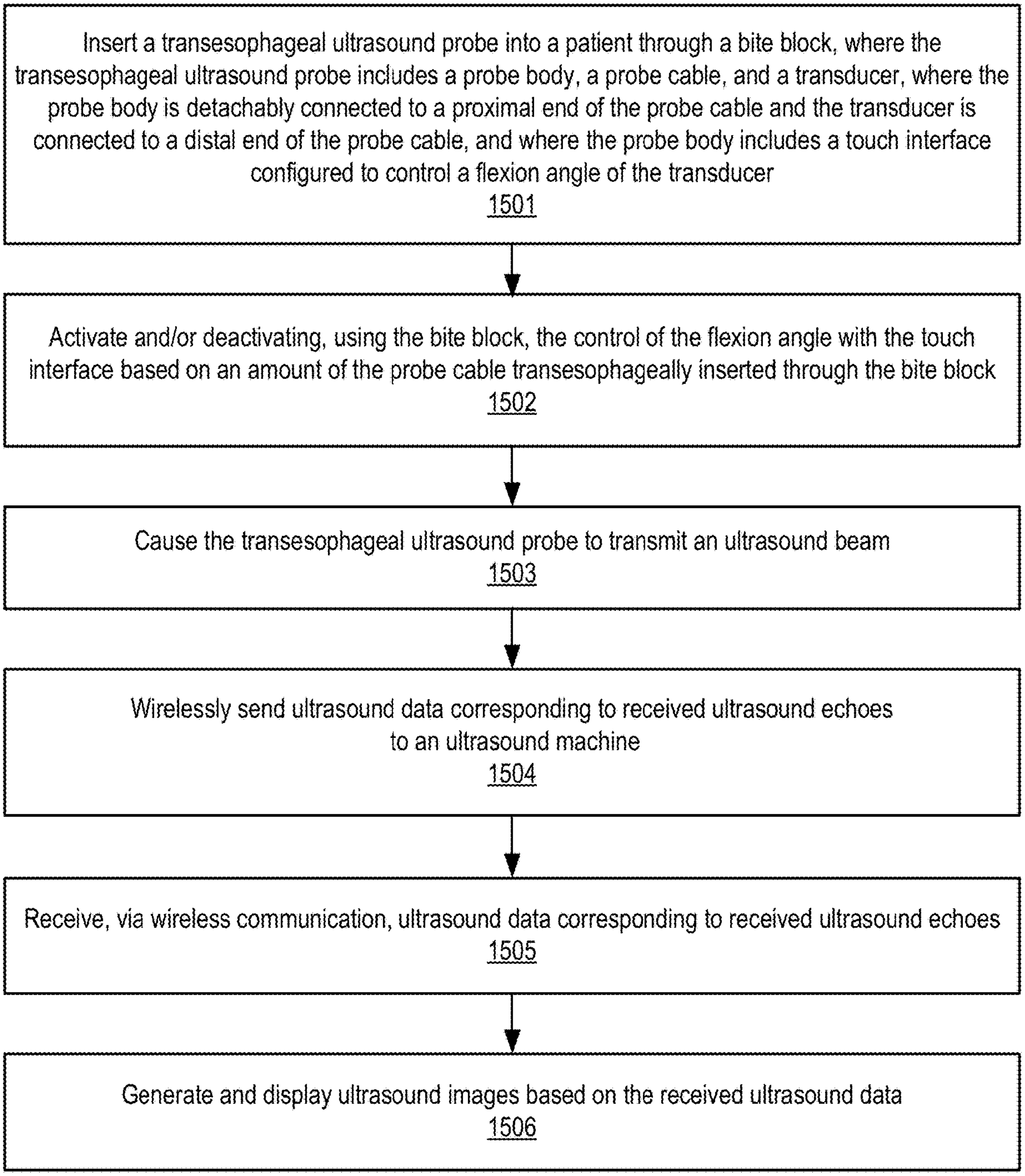
FIG. 15 is a data flow diagram of some embodiments of process for performing an ultrasound examination.

FIG. 15 illustrates a data flow diagram of some embodiments of process for performing an ultrasound examination. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, a transesophageal ultrasound system with an ultrasound machine and an ultrasound probe, such as, for example, described above.

Referring to FIG. 15, the process begins by inserting a transesophageal ultrasound probe into a patient through a bite block, where the transesophageal ultrasound probe includes a probe body, a probe cable, and a transducer, where the probe body is detachably connected to a proximal end of the probe cable and the transducer is connected to a distal end of the probe cable, and where the probe body includes a touch interface configured to control a flexion angle of the transducer (processing block 1501). In some embodiments, the bite block includes a locking mechanism configured to lock the probe cable and prevent positional drift of the transducer.

In some embodiments, the touch interface is configured to control an omniplane angle of ultrasound transmitted by the transducer. In some embodiments, the touch interface includes capacitive sensors configured to sense finger locations proximate to the touch interface, and the ultrasound machine includes a user interface configured to display a graphic representation of the touch interface with indications of the finger locations. In some embodiments, the ultrasound machine is implemented to activate a training mode during which the ultrasound machine displays training materials that describe control of the transducer with the touch interface and control of the ultrasound machine with the touch interface.

Processing logic in the bite block a bite block activating and/or deactivating the control of the flexion angle with the touch interface based on an amount of the probe cable transesophageally inserted through the bite block (processing block 1502). In some embodiments, the probe cable includes depth markings to visually indicate the amount of the probe cable transesophageally inserted.

Processing logic causes the transesophageal ultrasound probe to transmit an ultrasound beam (processing block 1503) and wirelessly sends ultrasound data corresponding to received ultrasound echoes to an ultrasound machine (processing block 1504).

Thereafter, processing logic of the ultrasound machine receives, via wireless communication, ultrasound data (processing block 1505) and generates and displays ultrasound images based on the received ultrasound data (processing block 1506). In some embodiments, the transesophageal ultrasound probe includes a temperature sensor configured to determine a temperature of the transducer, and the ultrasound machine includes a user interface configured to display the temperature.

FIG. 16 illustrates a data flow diagram of some embodiments of process for performing an ultrasound examination. The process can be performed by processing logic that can include hardware (e.g., circuitry, dedicated logic, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, a transesophageal ultrasound system with an ultrasound machine and an ultrasound probe, such as, for example, described above.

Referring to FIG. 16, the process begins by obtaining a transesophageal ultrasound probe, where the transesophageal ultrasound probe includes a probe body, a probe cable, and a transducer, where the probe body is detachably connected to a proximal end of the probe cable and the transducer is connected to a distal end of the probe cable, and further where the probe body includes a touch interface configured to control the transducer and an ultrasound machine (processing block 1601).

With the transesophageal ultrasound probe, using a bite block to guide the probe cable during transesophageal insertion of a patient and guard the probe cable from being bitten by the patient (processing block 1602). In some embodiments, the bite block is implemented to determine, during the transesophageal insertion, an amount of the probe cable transesophageally inserted and deactivate the control of the transducer with the touch interface based on the amount of the probe cable transesophageally inserted.

Subsequently, after guiding the transesophageal ultrasound probe through the bite block, disconnecting the probe body from the probe cable while the probe cable and the transducer remain transesophageally inserted (processing block 1603).

After disconnecting the probe body, holding and preventing movement of the proximal end of the probe cable, using a mount, when the probe body is disconnected from the probe cable, and the probe cable and the transducer remain transesophageally inserted (processing block 1604). In some embodiments, the mount includes a clamp configured to secure the mount to a patient bed.

Additional Ultrasound System Features

In some embodiments, the ultrasound machine is implemented to activate a training mode during which the ultrasound machine can display training materials on the display of the ultrasound machine (e.g., display 410 of FIG. 4). The training materials can describe controls of the probe with its integrated controls via the touch interface of the control panel and how those controls may be used in order to control the ultrasound machine.

In some embodiments, a hand sensor is used to easily orient a probe. For instance, the hand sensor can include a sleeve that goes over a user's finger or glove for their hand. In this case, the user can place a finger on the chest of the patient or some other location on the patient's body they are scanning with the TEE probe in order to direct the scan head of the probe to the desired location. In this way, rather than using the controls on the control panel of the probe, a user could, via a sensor in (or on) their hand, direct approach to target the correct anatomy.

There are a number of example embodiments described herein.

Example 1 is an ultrasound probe comprising: a transceiver configured to communicatively couple the ultrasound probe to an ultrasound machine; a probe body having a user interface with controls and a mode selector; and a transducer coupled to the probe body, wherein when the mode selector is in a first setting, the controls are configured to control the transducer, and when the mode selector is in a second setting, the controls are configured to control the ultrasound machine via the transceiver.

Example 2 is the ultrasound system of example 1 that the controls include one or more first controls and one or more second controls configured to control depth and gain of the ultrasound machine, respectively, when the mode selector is in the second setting.

Example 3 is the ultrasound system of example 1 that when the mode selector is in the first setting, the one or more first controls are configured to control anteflexion and retroflexion movement of the transducer.

Example 4 is the ultrasound system of example 3 that when the mode selector is in the first setting, the one or more second controls are configured to control omniplane left and omniplane right ultrasound transmission of the transducer.

Example 5 is the ultrasound system of example 2 that when the mode selector is in the second setting, the user interface is configured to illuminate a portion of the user interface to indicate the control of depth and gain of the ultrasound machine.

Example 6 is the ultrasound system of example 1 that the transducer includes a transducer cable implemented to couple the transducer to the probe body, wherein the controls include a reset selector configured to, when activated, mechanically return the transducer to a default angle relative to the transducer cable.

Example 7 is the ultrasound system of example 6 that the transducer cable is configured for esophageal insertion.

Example 8 is the ultrasound system of example 1 that the transceiver is configured to implement a wireless communication link to communicatively couple the ultrasound probe to the ultrasound machine.

Example 9 is the ultrasound system of example 1 that the probe body is implemented to disconnect from the transducer and detachably connect to an additional transducer that is of a different form factor than the transducer.

Example 10 is the ultrasound system of example 9 that the different form factor is based on one or more of a patient size, a patient age, and a patient gender.

Example 11 is the ultrasound system of example 9 that the additional transducer is of the different form factor by including an additional transducer cable that is a different length than a transducer cable of the transducer, the additional transducer cable configured to couple the additional transducer to the probe body.

Example 12 is an ultrasound system comprising: an ultrasound machine having a user interface configured to display an ultrasound image based on ultrasound data; and an ultrasound probe communicatively coupled to the ultrasound machine and configured to generate the ultrasound data, the ultrasound probe having: a probe body with a touch interface having controls and a mode selector; and a transducer coupled to the probe body; wherein when the mode selector is in a first setting, the controls are configured to control the transducer, the touch interface is configured to indicate the controls with first indicators, and the user interface is configured to display a graphic of the touch interface having the first indicators, wherein when the mode selector is in a second setting, the controls are configured to control the ultrasound machine, the touch interface is configured to indicate the controls with second indicators, and the user interface is configured to display a graphic of the touch interface having the second indicators.

Example 13 is the ultrasound system of example 12 that the controls include one or more first controls and one or more second controls configured to control depth and gain of the ultrasound machine, respectively, when the mode selector is in the second setting and, when the mode selector is in the first setting, the one or more first controls are configured to control anteflexion and retroflexion movement of the transducer and the one or more second controls are configured to control omniplane left and omniplane right ultrasound transmission of the transducer.

Example 14 is the ultrasound system of example 12 that the transducer includes a transducer cable implemented to couple the transducer to the probe body, a tip of the transducer is configured to move at an angle relative to the transducer cable based on the controls, and the user interface is configured to display an indicator of the angle.

Example 15 is the ultrasound system of example 14 that the indicator of the angle includes a graphic icon of the tip of the transducer and a portion of the transducer cable.

Example 16 is the ultrasound system of example 12 that the controls are configured to control an omniplane angle of ultrasound transmitted by the transducer, and the user interface is configured to display an indicator of the omniplane angle.

Example 17 is the ultrasound system of example 12 that the user interface is configured to: display one or more graphics representing flexion angles of the transducer for imaging different anatomies; and receive a user selection of an additional graphic of the one or more graphics; and the ultrasound probe is configured to move, responsive to the user selection, the transducer to a position corresponding to a flexion angle represented by the additional graphic.

Example 18 is an ultrasound system comprising: an ultrasound machine having a user interface configured to display an ultrasound image based on ultrasound data; and an ultrasound probe communicatively coupled to the ultrasound machine and configured to generate the ultrasound data, the ultrasound probe having: a probe body with a touch interface having controls and a mode selector; an ultrasound cable; and a transducer at one end of the ultrasound cable and coupled to the probe body via the ultrasound cable; wherein when the mode selector is in a first setting, the controls are configured to control a flexion angle of the transducer relative to the probe cable, and the user interface is configured to display an indicator of the flexion angle.

Example 19 is the ultrasound system of example 18 that when the mode selector is in a second setting, the controls are configured to control one or more imaging parameters of the ultrasound machine.

Example 20 is the ultrasound system of example 18 that the user interface is configured to display one or more graphics representing flexion angles of the transducer for imaging different anatomies, and receive a user selection of an additional graphic of the one or more graphics; the ultrasound machine includes a neural network configured to generate a target flexion angle based on the ultrasound image and an additional flexion angle represented by the additional graphic; and the ultrasound probe is configured to move the transducer to a position corresponding to the target flexion angle.

Example 21 is the ultrasound system of example 18 that the user interface is configured to display a graphic representation of the touch interface.

Example 22 is the ultrasound system of example 21 that the touch interface includes sensors configured to sense finger locations proximate to the touch interface, and the user interface is configured to display the graphic representation of the touch interface with indications of the finger locations.

Example 23 is the ultrasound system of example 18 that the user interface is configured to display a graphic representing view planes, and receive a user selection of a view plane represented by the graphic; and the ultrasound probe is implemented to configure the transducer to transmit ultrasound based on the view plane.

Example 24 is the ultrasound system of example 18 that the ultrasound machine includes a neural network configured to generate image quality measures corresponding to a range of angles offset from a view plane used to capture the ultrasound image, and the ultrasound machine is configured to change the view plane based on the image quality measures.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A method to operate an ultrasound probe and an ultrasound machine coupled to the ultrasound probe, the ultrasound probe comprising a probe body having a touch user interface comprising one or more first controls and one or more second controls and a mode selector having a first setting and a second setting; and a transducer coupled to the probe body, the transducer including a transducer head and a transducer cable coupled to the transducer head, the method comprising:

controlling a position of the transducer head relative to the transducer cable to perform a transesophageal echocardiogram (TEE) operation using at least one of one or more first controls and the one or more second controls when the mode selector is in the first setting, and controlling, using the at least one of one or more first controls and the one or more second controls, one or more imaging parameters of the ultrasound machine via a transceiver coupled to the ultrasound probe when the mode selector is in the second setting, wherein the at least one of one or more first controls and the one or more second controls are same controls for the first setting and the second setting.

2. The method as described in claim 1, wherein the one or more imaging parameters include at least one of a depth and a gain of the ultrasound machine.

3. The method as described in claim 2, wherein said controlling the position of the transducer head includes controlling an anteflexion movement and a retroflexion movement of the transducer head relative to the transducer cable, the method further comprising: when the mode selector is in the first setting, controlling the anteflexion movement and the retroflexion movement of the transducer head relative to the transducer cable that are associated with the TEE operation.

4. The method as described in claim 2, further comprising: when the mode selector is in the second setting, illuminating a portion of the touch user interface to indicate the control of the at least one of the depth and the gain of the ultrasound machine.

5. The method as described in claim 1, wherein the controls include a reset selector, the method further comprising: activating the reset selector; and mechanically returning the transducer head to a default angle relative to the transducer cable in response to activating the reset selector.

6. The method as described in claim 1, further comprising: wirelessly coupling the ultrasound probe to the ultrasound machine via a communication link using the transceiver.

7. The method as described in claim 1, further comprising: disconnecting the probe body from the transducer and detachably connect to an additional transducer that is of a different form factor than the transducer.

8. A method to operate an ultrasound system comprising an ultrasound machine having a user interface configured to display an ultrasound image based on ultrasound data; and an ultrasound probe communicatively coupled to the ultrasound machine and configured to generate the ultrasound data, the ultrasound probe having a probe body with a touch interface having controls and a mode selector having a first setting and a second setting, the controls comprising one or more first controls and one or more second controls; and a transducer coupled to the probe body, the transducer including a transducer head and a transducer cable coupled to the transducer head, the method comprising:

when the mode selector is in the first setting, controlling a position of the transducer head relative to the transducer cable to perform to perform a transesophageal echocardiogram (TEE) operation using at least one of the one or more first controls and the one or more second controls; and displaying the one or more first controls and the one or more second controls on the touch interface using first indicators; and when the mode selector is in the second setting, controlling one or more imaging parameters of the ultrasound machine using the at least one of the one or more first controls and the one or more second controls, and displaying the one or more first controls and the one or more second controls on the touch interface using second indicators, wherein the at least one of one or more first controls and the one or more second controls are same controls for the first setting and the second setting.

9. The method as described in claim 8, wherein the position of the transducer head is associated with an anteflexion movement and a retroflexion movement of the transducer head, and with an omniplane left rotation and an omniplane right rotation of the transducer head, wherein the one or more imaging parameters include depth and gain of the ultrasound machine and the one or more first controls are configured to control the depth and the one or more second controls are configured to control the gain when the mode selector is in the second setting and, when the mode selector is in the first setting, the one or more first controls are configured to control the anteflexion movement and the retroflexion movement of the transducer head relative to the transducer cable and the one or more second controls are configured to control the omniplane left rotation and the omniplane right rotation of the transducer head relative to the transducer cable.

10. The method as described in claim 8, further comprising:

coupling the transducer head to the probe body by the transducer cable;

moving the transducer head at an angle relative to the transducer cable by pressing at least one of the one or more first controls and the one or more second controls of the touch interface when the mode selector is switched to the first setting, and displaying, by the user interface, an indicator of the angle.

11. The method as described in claim 10, wherein the indicator of the angle includes a graphic icon of the transducer head and a portion of the transducer cable.

12. The method as described in claim 8, wherein said controlling the position of the transducer head includes controlling an omniplane rotation of the transducer head relative to the transducer cable, and controlling, using the at least one of the one or more first controls and the one or more second controls, an omniplane angle of ultrasound transmitted by the transducer head, and displaying, by the user interface, an indicator of the omniplane angle.

13. The method as described in claim 8, further comprising:

displaying, by the user interface, one or more graphics representing flexion angles of the transducer head for imaging different anatomies; and receiving, through the user interface, a user selection of an additional graphic of the one or more graphics; and moving, responsive to the user selection, the transducer head to a position corresponding to a flexion angle represented by the additional graphic.

14. A method to operate an ultrasound system, comprising an ultrasound machine having a user interface configured to display an ultrasound image based on ultrasound data, and an ultrasound probe communicatively coupled to the ultrasound machine and configured to generate the ultrasound data, the ultrasound probe having a probe body with a touch interface having one or more first controls and one or more second controls and a mode selector having a first setting and a second setting; a transducer including a transducer cable having a distal end and a proximate end; and a transducer head at the distal end of the transducer cable, wherein the proximate end of the transducer cable is coupled to the probe body, the method comprising:

when the mode selector is in the first setting, controlling a flexion angle of the transducer relative to the transducer cable for the TEE operation using at least one of the one or more first controls and the one or more second controls; and displaying, by the user interface, an indicator of the flexion angle;

when the mode selector is in the second setting, controlling one or more imaging parameters of the ultrasound machine using the at least one of the one or more first controls and the one or more second controls, wherein the at least one of one or more first controls and the one or more second controls are same controls for the first setting and the second setting.

15. The method as described in claim 14, wherein the one or more imaging parameters include at least one of depth and gain of the ultrasound machine.

16. The method as described in claim 14, further comprising:

displaying, by the user interface, one or more graphics representing flexion angles of the transducer head for imaging different anatomies;

receiving, through the user interface, a user selection of an additional graphic of the one or more graphics;

generating, using a neural network, a target flexion angle based on the ultrasound image and an additional flexion angle represented by the additional graphic; and moving, using the ultrasound probe, the transducer head to the position corresponding to the target flexion angle.

17. The method as described in claim 14, further comprising:

displaying, by the user interface, a graphic representation of the touch interface.

18. The method as described in claim 17, further comprising sensing, by a sensor coupled to the touch interface, finger locations proximate to the touch interface; and displaying, by the user interface, the graphic representation of the touch interface with indications of the finger locations.

19. The method as described in claim 14, further comprising:

displaying, by the user interface, a graphic representing view planes;

receiving, through the user interface, a user selection of a view plane represented by the graphic; and configuring the transducer head to transmit ultrasound based on the view plane.

20. The method as described in claim 14, further comprising:

generating, by a neural network coupled to the ultrasound machine, image quality measures corresponding to a range of angles offset from a view plane used to capture the ultrasound image; and changing the view plane based on the image quality measures.

* * * * *